(12) United States Patent
Al-Mahmood et al.

(10) Patent No.: US 9,206,236 B2
(45) Date of Patent: *Dec. 8, 2015

(54) PEPTIDES FOR TREATING CANCER

(75) Inventors: Salman Al-Mahmood, Paris (FR);
Sylvie Colin, Paris (FR)

(73) Assignee: Gene Signal International SA, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/996,973

(22) PCT Filed: Dec. 21, 2011

(86) PCT No.: PCT/EP2011/073606
§ 371 (c)(1),
(2), (4) Date: Jun. 21, 2013

(87) PCT Pub. No.: WO2012/085096
PCT Pub. Date: Jun. 28, 2012

(65) Prior Publication Data
US 2013/0274202 A1     Oct. 17, 2013

Related U.S. Application Data

(63) Continuation-in-part of application No. 12/974,958, filed on Dec. 21, 2010, now Pat. No. 8,383,591.

(30) Foreign Application Priority Data

Dec. 21, 2010  (EP) .................................... 10196278

(51) Int. Cl.
| | | |
|---|---|---|
| *A61K 38/08* | (2006.01) | |
| *C07K 14/00* | (2006.01) | |
| *C07K 7/06* | (2006.01) | |
| *A61K 38/10* | (2006.01) | |
| *A61K 38/16* | (2006.01) | |
| *A61K 45/06* | (2006.01) | |
| *C07K 7/08* | (2006.01) | |
| *A61K 38/00* | (2006.01) | |

(52) U.S. Cl.
CPC .............. *C07K 14/001* (2013.01); *A61K 38/10* (2013.01); *A61K 38/16* (2013.01); *A61K 45/06* (2013.01); *C07K 7/06* (2013.01); *C07K 7/08* (2013.01); *A61K 38/00* (2013.01)

(58) Field of Classification Search
None
See application file for complete search history.

(56) References Cited

U.S. PATENT DOCUMENTS 5,801,149 A * 9/1998 Shoelson .................. 514/8.2

FOREIGN PATENT DOCUMENTS

| WO | 9610629 | 4/1996 |
| WO | 0075167 | 12/2000 |
| WO | 2005035003 | 4/2005 |

OTHER PUBLICATIONS

Giubellino et al. "Grb2 signaling in cell motility and cancer" Expert Opin. Ther. Targets (2008) 12(8):1021-1033.*
Atabey et al. "Potent Blockade of Hepatocyte Growth Factor-stimulated Cell Motility, Matrix Invasion and Branching Morphogenesis by Antagonists of Grb2 Src Homology 2 Domain Interactions" J. Biol. Chem. 2001, 276:14308-14314.*
Soriano et al. "Inhibition of angiogenesis by growth factor receptor bound protein 2-Src homology 2 domain bound antagonists" Mol Cancer Ther 2004;3:1289-1299.*
Giubellino et al. "Inhibition of Tumor Metastasis by a Growth Factor Receptor Bound Protein 2 Src Homology 2 Domain-Binding Antagonist," Cancer Res 2007; 67: (13). Jul. 1, 2007, pp. 6012-6016.*
Chen et al. "Effects of Peptidic Antagonists of Grb2-SH2 on Human Breast Cancer Cells" Protein & Peptide Letters, 2010, 17, 44-53.*
Al-Mahmood et al., "Potent in Vivo Antiangiogenic Effects of GS-101 (5'-TATCCGGAGGGCTCGCCATGCTGCT-3'), an Antisense Oligonucleotide Preventing the Expression of Insulin Receptor Substrate-1," *JPET*, 329(2): 496-504, 2009.
Balsari et al., "Combination of a CpG-oligodeoxynucleotide and a toposomerase I inhibitor in the therapy of human tumour xenografts," *Eur. J. Cancer*, 40:1275-1281, 2004.
Bunney et al., "Phosphoinositide signalling in cancer: beyond PI3K and PTEN," *Nat. Rev.*, 10(5):342-352, 2010.
Cantley, "The phosphoinositide 3-kinase pathway," *Science*, 296:1655-1657, 2002.
Carpenter and Cantley, "Phosphoinositide kinases," *Curr Opin. Cell Biol.*, 8:153-158, 1996.
Fry, "Structure, regulation and function of phosphoinositide 3-kinases," *Biochim. Biophys. Acta.*, 1226:237-268, 1994.
Kotani et al., "Involvement of phosphoinositide 3-kinase in insulin- or IGF-1-induced membrane ruffling," *EMBO J.*, 13(10):2313-2321, 1994.
White et al., "The insulin signaling system," *Journal of Biological Chemistry*, 269(7):1-4, 1994.
Yonesawa et al., "Insulin-dependent formation of a complex containing an 85-kDa subunit of phosphatidylinositol 3-kinase and tyrosine-phosphorylated insulin receptor substrate 1," *J Biol. Chem.*, 267(367):25958-25965, 1992.
International Search Report dated Jun. 12, 2012 in the corresponding PCT application WO2012/085096.
Cursiefen, et al. "GS-101 Antisense Oligonucleotide Eye Drops Inhibit Corneal Neovasculatization: Interim Results of a Randomized Phase II Trial" Ophthalmology, vol. 116, No. 9, Sep. 2009, pp. 1630-1637.
Kimoto and Kubota "Anti-VEGF Agents for Ocular Angiogenesis and Vascular Permeability" J Ophthalmology, vol. 2012; 2012:852183. Doi: 10.1155/2012/852183. Epub Nov. 3, 2011.

* cited by examiner

*Primary Examiner* — Christina Bradley
(74) *Attorney, Agent, or Firm* — Norton Rose Fulbright US LLP

(57) ABSTRACT

The present invention relates to peptide from 4 to 50 amino acids comprising a phosphorylated pYX$_1$X$_2$X$_1$ motif (SEQ ID NO: 1), wherein each X$_1$ independently is M or Nle and X$_2$ is any amino acid, pharmaceutical compositions comprising said peptide and use thereof for treating cancer.

5 Claims, 5 Drawing Sheets

A

B

PEPTIDES FOR TREATING CANCER

CROSS-REFERENCE TO RELATED APPLICATIONS

This application is a national phase application under 35 U.S.C. §371 of International Application No. PCT/EP2011/073606 filed 21 Dec. 2011, which claims priority to U.S. patent application Ser. No. 12/974,958 filed 21 Dec. 2010, and European Patent Application No. 10196278.5 filed 21 Dec. 2010. The entire contents of each of the above-referenced disclosures is specifically incorporated herein by reference without disclaimer.

FIELD OF THE INVENTION

The present invention relates to peptides, compositions comprising thereof and use thereof for treating cancer.

BACKGROUND OF THE INVENTION

Many growth factors and hormones such as nerve growth factor (NGF), platelet derived growth factor (PDGF), epidermal growth factor (EGF) and insulin mediate their signals through interactions with cell surface tyrosine kinase receptors. The transduction of extracellular signals across the membrane, initiated by ligand binding, leads to the propagation of multiple signaling events which ultimately control target biochemical pathways within the cell.

The phosphatidylinositol 3-kinases (PI3Ks) represent a ubiquitous family of heterodimeric lipid kinases that are found in association with the cytoplasmic domain of hormone and growth factor receptors and oncogene products. PI3Ks act as downstream effectors of these receptors, are recruited upon receptor stimulation and mediate the activation of second messenger signaling pathways through the production of phosphorylated derivatives of inositol (Fry, Biochim. Biophys. Acta., 1994, 1226:237-268).

The class I PI3Ks are composed of a Src homology-2 domain-containing an 85 kDa regulatory subunit (p85) and a 110-kDa catalytic subunit (p110), which catalyze the phosphorylation of phosphotidylinositol at the D3 position of the inositol ring (Cantley, Science 296:1655-1657 (2002); Carpenter and Cantley, Curr. Opin. Cell Biol., 8:153-8 (1996)).

PI3Ks plays a central role in a broad range of biological effects including growth factor mediated cell transformation, mitogenesis, protein trafficking, cell survival and proliferation, DNA synthesis, apoptosis, neurite outgrowth and insulin-stimulated glucose transport (reviewed in Fry, Biochim. Biophys. Acta., 1994, 1226, 237-268). Its apparent involvement in so many disparate signaling pathways suggests that it may provide a more general, facilitative, signaling function, such as targeting an active complex, rather than directly controlling these myriad events.

Inhibitors of proteins that are involved in the PI3K signaling have been suggested as therapeutic agents. Examples of said inhibitors include wortmannin, demethoxyviridin, quercetin and LY294002. These inhibitors primarily target the p110 subunit and display toxicity and short half-life which limit their use in clinical trials.

An alternative approach to these inhibitors has been to specifically inhibit the expression of important pathways proteins by RNA interference, such as specific inhibition of p85 expression by siRNA.

The aim of the present invention was to find inhibitors of PI3K signaling. Preferably, said inhibitors would present the following advantages: high stability, a cell penetration/diffusion better than siRNAs, and a half-life better than siRNAs.

The inventors made the surprising observation that peptides having a phosphorylated $YX_1X_2X_1$ motif as defined here after are capable of reducing tumor size in vivo. Sequences having phosphotyrosine residues in the context of the motif YMXM are known to bind to SH2 domains. p85 is described to possess two SH2 domains and the binding of these SH2 domains to phosphotyrosine residues in the context of the motif YMXM is described to activate p85 and p110 leading to the catalyzation of the phosphorylation of phosphatidylinositol (PdtIns) producing PtdIns(3), $PtdIns(3,4)P_2$ and $PtdIns(3,4,5)P_3$.

Synthetic peptides containing a phosphorylated YMXM motif are known in the art to activate PI3K in vitro (White et al. 1994 The Journal of Biological Chemistry 269 (7):1-4). As activation of PI3K signaling is known to be implicated in cancer development, the person skilled in the art would thus not have been induced to use peptides activating PI3K signaling for treating cancer.

SUMMARY

One object of the invention is a peptide comprising a phosphorylated $pYX_1X_2X_1$ motif (SEQ ID NO: 1),
wherein each $X_1$ independently is M or Nle and X2 is any amino acid,
wherein said peptide comprises from 4 to 50 amino acids, and
wherein said peptide is not SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 29, SEQ ID NO: 30, SEQ ID NO: 31 or SEQ ID NO: 32.

In one embodiment, the peptide of the invention is not SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 29, SEQ ID NO: 30, SEQ ID NO: 31, SEQ ID NO: 32, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63 or SEQ ID NO: 64.

In one embodiment of the invention, said peptide comprises from 6 to 20 amino acids and comprises a phosphorylated $GpYX_1FX_1S$ motif (SEQ ID NO: 15), wherein each $X_1$ independently is M or Nle.

In another embodiment of the invention, said peptide comprises from 6 to 20 amino acids and comprises a phosphorylated $EpYX_1NX_1D$ motif (SEQ ID NO: 19), wherein each $X_1$ independently is M or Nle.

In another embodiment of the invention, said peptide comprises from 6 to 20 amino acids and comprises a phosphorylated $GpYX_1PX_1S$ motif (SEQ ID NO: 14), wherein each $X_1$ independently is M or Nle.

In another embodiment of the invention, said peptide comprises from 6 to 20 amino acids and comprises a phosphorylated $DpYX_1FX_1S$ motif (SEQ ID NO: 16), wherein each $X_1$ independently is M or Nle.

In another embodiment of the invention, said peptide comprises from 6 to 20 amino acids and comprises a phosphorylated $GpYX_1MX_1S$ motif (SEQ ID NO: 17), wherein each $X_1$ independently is M or Nle.

In another embodiment of the invention, said peptide comprises from 6 to 20 amino acids and comprises a phosphorylated DpYX$_1$NX$_1$S motif (SEQ ID NO: 18), wherein each X$_1$ independently is M or Nle.

In another embodiment of the invention, said peptide comprises from 6 to 20 amino acids and comprises a phosphorylated DpYX$_1$TX$_1$Q motif (SEQ ID NO: 20), wherein each X$_1$ independently is M or Nle.

Another object of the invention is a pharmaceutical composition comprising a peptide from 4 to 50 amino acids comprising a phosphorylated pYX$_1$X$_2$X$_1$ motif (SEQ ID NO: 1), wherein each X$_1$ independently is M or Nle and X$_2$ is any amino acid.

In one embodiment of the invention, said peptide comprises from 6 to 20 amino acids and a phosphorylated GpYX$_1$X$_2$X$_1$S motif (SEQ ID NO: 33), wherein each X$_1$ independently is M or Nle and X$_2$ is P, F or M.

In another embodiment of the invention, said peptide comprises from 6 to 20 amino acids and a phosphorylated DpYX$_1$X$_2$X$_1$S motif (SEQ ID NO: 34), wherein each X$_1$ independently is M or Nle and X$_2$ is P or N.

In another embodiment of the invention, said peptide comprises from 6 to 20 amino acids and a phosphorylated EpYX$_1$NX$_1$D motif (SEQ ID NO: 35), wherein each X$_1$ independently is M or Nle.

In another embodiment of the invention, said peptide comprises from 6 to 20 amino acids and a phosphorylated DpYX$_1$TX$_1$Q motif (SEQ ID NO: 36), wherein each X$_1$ independently is M or Nle.

Another object of the present invention is a pharmaceutical composition as described here above for treating cancer.

Another object of the present invention is a pharmaceutical composition as described here above for treating an angiogenesis-related disease.

Another object of the present invention is a pharmaceutical composition as described here above further comprising at least one cytotoxic, chemotherapeutic or anti-cancer agent.

DETAILED DESCRIPTION OF THE INVENTION

Definitions

As used herein, the term "peptide" refers to an amino acid sequence from 2 amino acids to 50 amino acids. Preferably, the peptide comprises from 3 amino acids to 45 amino acids, more preferably from 3 to 40 amino acids, even more preferably from 4 to 30 amino acids. Particularly preferred embodiments include peptides comprising from 4 to 20 amino acids, such as from 5 to 15 amino acids or from 5 to 10 amino acids. An "isolated" peptide refers to one that has been removed from its natural environment or to one that has been designed by a person skilled in the art. As used herein, "amino acids" are represented by their full name, their three letter code or their one letter code as well known in the art. Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. The term "amino acids" includes both natural and synthetic amino acids, and both D and L amino acids. "Standard amino acid" or "naturally occurring amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. For example, naphtlylalanine can be substituted for tryptophan to facilitate synthesis. Other synthetic amino acids that can be substituted include, but are not limited to, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl.

As used herein, "amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The peptides of the invention may comprise naturally standard amino acids or non-standard amino acids. Peptide mimetics include peptides having the following modifications: i) peptides wherein one or more of the peptidyl —C(O) NR— linkages (bonds) have been replaced by a non-peptidyl linkage such as a —CH$_2$-carbamate linkage (—CH$_2$OC(O) NR—), a phosphonate linkage, a —CH2-sulfonamide (—CH2-S(O)2NR—) linkage, a urea (—NHC(O)NH—) linkage, a —CH$_2$-secondary amine linkage, or with an alkylated peptidyl linkage (—C(O)NR—) wherein R is C$_1$-C$_4$ alkyl; ii) peptides wherein the N-terminus is derivatized to a —NRR$^1$ group, to a —NRC(O)R group, to a —NRC(O)OR group, to a —NRS(O)$_2$R group, to a —NHC(O)NHR group where R and R$^1$ are hydrogen or C$_1$-C$_4$ alkyl with the proviso that R and R$^1$ are not both hydrogen; iii) peptides wherein the C terminus is derivatized to —C(O)R$^2$ where R$^2$ is selected from the group consisting of C$_1$-C$_4$ alkoxy, and —NR$^3$R$^4$ where R$^3$ and R$^4$ are independently selected from the group consisting of hydrogen and C$_1$-C$_4$ alkyl.

As used herein, the term "conservative amino acid substitution" is defined herein as an amino acid exchange within one of the following five groups:

I. Small aliphatic, nonpolar or slightly polar residues: Ala, Ser, Thr, Pro, Gly;

II. Polar, negatively charged residues and their amides: Asp, Asn, Glu, Gln;

III. Polar, positively charged residues: His, Arg, Lys;

IV. Large, aliphatic, nonpolar residues: Met, Leu, Be, Val, Cys

V. Large, aromatic residues: Phe, Tyr, Trp.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease. A "therapeutic" treatment is a treatment administered to a subject who exhibits signs of pathology for the purpose of diminishing or eliminating those signs. A "therapeutically effective amount" of a compound is that amount of compound which is sufficient to provide a beneficial effect to the subject to which the compound is administered.

The Invention

One object of the invention is a peptide comprising a phosphorylated pYX$_1$X$_2$X$_1$ motif (SEQ ID NO: 1).

According to the invention, the tyrosine Y is phosphorylated (pY).

According to the invention, each amino acid X$_1$ in the phosphorylated pYX$_1$X$_2$X$_1$ motif independently corresponds to M (Methionine) or Nle (Norleucine). The peptide of the invention thus comprises a phosphorylated pYMX$_2$M motif, a pYMX$_2$Nle motif, a pYNleX$_2$M motif or a pYNleX$_2$Nle motif. Preferably, the X$_1$ at Y+1 position is independently M or Nle and the X$_1$ at Y+3 position is M.

According to the invention, the amino acid X$_2$ in the phosphorylated pYX$_1$X$_2$X$_1$ motif corresponds to any amino acid, preferably any naturally occurring amino acid. Preferably, X$_2$ is selected in the group comprising P, M, N, T, K and F. More preferably, X$_2$ is selected in the group comprising F, N and T.

In one embodiment of the invention, said peptide is not DDGpYMPMSPGV (SEQ ID NO: 2), NGDpYMPMSPGV (SEQ ID NO: 3), PNGpYMMMSPSG (SEQ ID NO: 4), TGDpYMNMSPVG (SEQ ID NO: 5), SEEpYMNMDLGP (SEQ ID NO: 6), KKHTDDGpYMPMSPGVA (SEQ ID NO: 7), RKGNGDpYMPMSPKSV (SEQ ID NO: 8), KKRVD-PNGpYMMMSPSGS (SEQ ID NO: 9), KKKLPATGD-pYMNMSPVGD (SEQ ID NO: 10), KKGSEEpYMNM-DLGPGR (SEQ ID NO: 11), KKSRGDpYMTMQIG (SEQ ID NO: 12), KKSRGNpYMTMQIG (SEQ ID NO: 13), EEEYMpPMEDLY (SEQ ID NO: 29), DGGpYMDMSKDE (SEQ ID NO: 30), KKKEEEEEpYMPMEDL (SEQ ID NO: 31), KKSRGDpYNleTMQIG (SEQ ID NO: 32), TDDG-pYMPMSPGV (SEQ ID NO: 41), DPNGpYMMMSPSG (SEQ ID NO: 43), GNGDpYMPMSPKS (SEQ ID NO: 44), RENEpYMPMAPQIH (SEQ ID NO: 45), EEEEpYMPMEDLYL (SEQ ID NO: 46), TDDGpYMPM-SPGVA (SEQ ID NO: 47), GNGDpYMPMSPKSV (SEQ ID NO: 48), SDGGpYMDMSKDES (SEQ ID NO: 49), RDG-pYMTMQIG (SEQ ID NO: 50), IDVpYMIMVK (SEQ ID NO: 51), DGGpYMDMSKDE (SEQ ID NO: 52), HSDpYM-NMTPR (SEQ ID NO: 53), NGDpYMPMSPKS (SEQ ID NO: 54), GDpYMPMSPKS (SEQ ID NO: 55), DpYMPM-SPKS (SEQ ID NO: 56), pYMPMSPKS (SEQ ID NO: 57), pYMPMSP (SEQ ID NO: 58), pYMPMS (SEQ ID NO: 59), pYMPM (SEQ ID NO: 60), pYMPMSPAS (SEQ ID NO: 61), pYMPMSAKS (SEQ ID NO: 62), pYMPMAPKS (SEQ ID NO: 63) or pYMAMSPKS SEQ ID NO: 64.

In one embodiment of the invention, said peptide is not GNGDpYMPMDPKS (SEQ ID NO: 42).

In one embodiment of the invention, said peptide comprises from 4 to 50 amino acids. In another embodiment of the invention, said peptide comprises from 4 to 40 amino acids. In another embodiment of the invention, said peptide comprises from 4 to 30 amino acids. In another embodiment of the invention, said peptide comprises from 5 to 25 amino acids. In another embodiment of the invention, said peptide comprises from 5 to 20 amino acids. In another embodiment of the invention, said peptide comprises from 5 to 18 amino acids. In another embodiment of the invention, said peptide comprises from 5 to 15 amino acids. In another embodiment of the invention, said peptide comprises from 5 to 14 amino acids. In another embodiment of the invention, said peptide comprises from 5 to 13 amino acids. In another embodiment of the invention, said peptide comprises from 5 to 12 amino acids. In another embodiment of the invention, said peptide comprises from 5 to 11 amino acids. In another embodiment of the invention, said peptide comprises from 5 to 10 amino acids. In another embodiment of the invention, said peptide comprises from 5 to 9 amino acids. In another embodiment of the invention, said peptide comprises from 5 to 8 amino acids. In another embodiment of the invention, said peptide comprises from 5 to 7 amino acids. In another embodiment of the invention, said peptide comprises 6 amino acids.

In another embodiment of the invention, said peptide consists of or consists essentially of 5 to 50 amino acids, of 5 to 40 amino acids, of 5 to 30 amino acids, of 5 to 25 amino acids, of 5 to 20 amino acids, of 5 to 18 amino acids, of 5 to 15 amino acids, of 5 to 14 amino acids, of 5 to 13 amino acids, of 5 to 12 amino acids, of 5 to 11 amino acids, of 5 to 10 amino acids, of 5 to 9 amino acids, of 5 to 8 amino acids, of 5 to 7 amino acids, of 6 amino acids.

In one embodiment of the invention, said peptide has 50, 40, 30, 20 amino acids length, 19, 18, 17, 16, 15, 14, 13, 12, 11, 10, 9, 8, 7, 6 amino acids length and comprises the phosphorylated GpYX$_1$PX$_1$S motif (SEQ ID NO: 14), wherein each X$_1$ independently is M or Nle.

In another embodiment of the invention, said peptide has 50, 40, 30, 20 amino acids length, 19, 18, 17, 16, 15, 14, 13, 12, 11, 10, 9, 8, 7, 6 amino acids length and comprises the phosphorylated GpYX$_1$FX$_1$S motif (SEQ ID NO: 15), wherein each X$_1$ independently is M or Nle.

In another embodiment of the invention, said peptide has 50, 40, 30, 20 amino acids length, 19, 18, 17, 16, 15, 14, 13, 12, 11, 10, 9, 8, 7, 6 amino acids length and comprises the phosphorylated DpYX$_1$PX$_1$S motif (SEQ ID NO: 16), wherein each X$_1$ independently is M or Nle.

In another embodiment of the invention, said peptide has 50, 40, 30, 20 amino acids length, 19, 18, 17, 16, 15, 14, 13, 12, 11, 10, 9, 8, 7, 6 amino acids length and comprises the phosphorylated GpYX$_1$MX$_1$S motif (SEQ ID NO: 17), wherein each X$_1$ independently is M or Nle.

In another embodiment of the invention, said peptide has 50, 40, 30, 20 amino acids length, 19, 18, 17, 16, 15, 14, 13, 12, 11, 10, 9, 8, 7, 6 amino acids length and comprises the phosphorylated DpYX$_1$NX$_1$S motif (SEQ ID NO: 18), wherein each X$_1$ independently is M or Nle.

In another embodiment of the invention, said peptide has 50, 40, 30, 20 amino acids length, 19, 18, 17, 16, 15, 14, 13, 12, 11, 10, 9, 8, 7, 6 amino acids length and comprises the phosphorylated EpYX$_1$NX$_1$D motif (SEQ ID NO: 19), wherein each X$_1$ independently is M or Nle.

In another embodiment of the invention, said peptide has 50, 40, 30, 20 amino acids length, 19, 18, 17, 16, 15, 14, 13, 12, 11, 10, 9, 8, 7, 6 amino acids length and comprises the phosphorylated DpYX$_1$TX$_1$Q motif (SEQ ID NO: 20), wherein each X$_1$ independently is M or Nle.

In one embodiment of the invention, said peptide is PDSSTLHTDDGpYX$_1$PX$_1$SPGVAPVPSGRKGSG (SEQ ID NO: 21) or a fragment of 20, 19, 18, 17, 16, 15, 14, 13, 12, 11, 10, 9, 8, 7 or 6 amino acids comprising the phosphorylated pYX$_1$PX$_1$ motif, wherein each X$_1$ independently is M or Nle.

In another embodiment of the invention, said peptide is PDSSTLHTDDGpYX$_1$FX$_1$SPGVAPVPSGRKGSG (SEQ ID NO: 22) or a fragment of 20, 19, 18, 17, 16, 15, 14, 13, 12, 11, 10, 9, 8, 7 or 6 amino acids comprising the phosphorylated pYX$_1$FX$_1$ motif, wherein each X$_1$ independently is M or Nle.

In another embodiment of the invention, said peptide is PVPSGRKGSGDpYX$_1$PX$_1$SPKSVSAPQQIINPI (SEQ ID NO: 23) or a fragment of 20, 19, 18, 17, 16, 15, 14, 13, 12, 11, 10, 9, 8, 7 or 6 amino acids comprising the phosphorylated pYX$_1$PX$_1$ motif, wherein each X$_1$ independently is M or Nle.

In another embodiment of the invention, said peptide is RRHPQRVDPNGpYX$_1$MX$_1$SPSGGCSPDIGGGPS (SEQ ID NO: 24) or a fragment of 20, 19, 18, 17, 16, 15, 14, 13, 12, 11, 10, 9, 8, 7 or 6 amino acids comprising the phosphorylated pYX$_1$MX$_1$ motif, wherein each X$_1$ independently is M or Nle.

In another embodiment of the invention, said peptide is SGGKLLPCTGDpYX$_1$NX$_1$SPVGDSNTSSPSDCY (SEQ ID NO: 25) or a fragment of 20, 19, 18, 17, 16, 15, 14, 13, 12, 11, 10, 9, 8, 7 or 6 amino acids comprising the phosphorylated pYX$_1$NX$_1$ motif, wherein each X$_1$ independently is M or Nle.

In another embodiment of the invention, said peptide is PREEETGTEEpYX$_1$KX$_1$DLGPGRRAAWQESTGV (SEQ ID NO: 26) or a fragment of 20, 19, 18, 17, 16, 15, 14, 13, 12, 11, 10, 9, 8, 7 or 6 amino acids comprising the phosphorylated pYX$_1$KX$_1$ motif, wherein each X$_1$ independently is M or Nle.

In another embodiment of the invention, said peptide is PREEETGTEEpYX$_1$NX$_1$DLGPGRRAAWQESTGV (SEQ ID NO: 27) or a fragment of 20, 19, 18, 17, 16, 15, 14, 13, 12, 11, 10, 9, 8, 7 or 6 amino acids comprising the phosphorylated pYX$_1$NX$_1$ motif, wherein each X$_1$ independently is M or Nle.

In another embodiment of the invention, said peptide is AVPSSRGDpYX$_1$TX$_1$QMSCPRQSYVDTSPAAPV (SEQ ID NO: 28) or a fragment of 20, 19, 18, 17, 16, 15, 14, 13, 12, 11, 10, 9, 8, 7 or 6 amino acids comprising the phosphorylated pYX$_1$TX$_1$ motif, wherein each X$_1$ independently is M or Nle.

The peptides described herein can be produced synthetically by chemical synthesis or enzymatic synthesis as it is well known in the art. Alternatively, nucleotide sequences encoding the peptides of the invention can be introduced into a protein expression vector and produced in a suitable host organism (e.g., bacteria, insect cells, etc), then purified. An additional polypeptide ("tag") can be added on for the purpose of purifying or identifying or purifying the peptides. Protein tags make it possible, for example, for the polypeptides to be adsorbed, with high affinity, to a matrix, and for the matrix then to be washed stringently with suitable buffers without the complex being eluted to any significant extent, and for the adsorbed complex subsequently to be eluted selectively. Examples of protein tags which are known to the skilled person are a (His)$_6$ tag, a Myc tag, a FLAG tag, a haemagglutinin tag, a glutathione transferase (GST) tag, intein having an affinity chitin-binding tag or maltose-binding protein (MBP) tag. These protein tags can be located N-terminally, C-terminally and/or internally.

One object of the invention is the peptides as described here above, said peptides being modified.

The peptides provided herein can be modified by means well-known in the art.

For example, the peptides can be modified by the addition of one or more functional groups such as phosphate, acetate, or various lipids and carbohydrates. The peptides of the invention can also exist as peptide derivatives. The term "peptide derivative" refers to compound having an amino group (—NH—), and more particularly, a peptide bond. Peptides may be regarded as substituted amides. Like the amide group, the peptide bond shows a high degree of resonance stabilization. The C—N single bond in the peptide linkage has typically about 40 percent double-bond character and the C=O double bond about 40 percent single-bond character. "Protecting groups" are those groups that prevent undesirable reactions (such as proteolysis) involving unprotected functional groups. Specific examples of amino protecting groups include formyl; trifluoroacetyl; benzyloxycarbonyl; substituted benzyloxycarbonyl such as (ortho- or para-) chlorobenzyloxycarbonyl and (ortho- or para-) bromobenzyloxycarbonyl; and aliphatic oxycarbonyl such as t-butoxycarbonyl and t-amiloxycarbonyl. The carboxyl groups of amino acids can be protected through conversion into ester groups. The ester groups include benzyl esters, substituted benzyl esters such as methoxybenzyl ester; alkyl esters such as cyclohexyl ester, cycloheptyl ester or t-butyl ester. The guanidino moiety may be protected by nitro; or arylsulfonyl such as tosyl, methoxybenzensulfonyl or mesitylenesulfonyl, even though it does not need a protecting group. The protecting groups of imidazole include tosy, benzyl and dinitrophenyl. The indole group of tryptophan may be protected by formyl or may not be protected.

The modification of the peptides aims in particular to improve their life time in vivo. One type of modification is the addition to the N or C termini of the peptides of polyethylene glycol (PEG). PEG is known by the person skilled in the art to have many properties that make it an ideal carrier for peptides such as high water solubility, high mobility in solution and low immunogenicity. This modification also protects the peptides from exopeptidases and therefore increases their overall stability in vivo.

The other modifications used to prevent degradation of the peptides by endopeptidases or exopeptidases include N-terminal modifications such as acetylation or glycosylation, C-terminal modifications such as amidation and use of unnatural amindo acids (β-amino and α-trifluoromethyl amino acids) at particularly sites within the peptides.

Another alternative to increase peptide molecular size is the genetic fusion of the peptides to the Fc domain of human gamma immunoglobulin or the fusion of the peptides to albumin.

Another object of the invention is a pharmaceutical composition comprising at least one of the peptides as described here above in combination with pharmaceutically acceptable excipients, wherein said peptide comprises a phosphorylated pYX$_1$X$_2$X$_1$ motif (SEQ ID NO: 1), wherein each X$_1$ independently is M or Nle and X$_2$ is any amino acid, preferably any naturally occurring amino acid.

The term "pharmaceutically acceptable" refers to compounds and compositions which may be administered to mammals without undue toxicity. Accordingly, a "Pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by FDA Office of Biologics standards.

Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, for example, BHA, BHT, citric acid, ascorbic acid, tetracycline, and the like.

Other examples of pharmaceutically acceptable excipients that may be used in the composition of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment, the composition of the invention may comprise some excipients, such as, for example, surfactants (e.g. hydroxypropylcellulose); suitable carriers, such as, for example, solvents and dispersion media containing, for example, water, ethanol, polyol (e.g. glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextran 40, dextran 70, dextrose, glycerin, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, ydroxmethylpropylcellulose, lanolin, methylcellulose, petrolatum, polyethylene glycol, polyvinyl alcohol, polyvinylpyrrolidone, carboxymethylcellulose; and the like.

In one embodiment, the composition may comprise a pharmaceutically acceptable salt of the peptide.

Examples of the pharmaceutically acceptable salt include salts with inorganic bases, salts with organic bases, salts with inorganic acids, salts with organic acids, salts with basic or acidic amino acids and the like. Examples of the salt with an inorganic base include alkali metal salts, such as a sodium salt and a potassium salt; an alkaline earth metal salt such as a calcium salt and a magnesium salt; an aluminum salt; and an ammonium salt. Examples of the salt with an organic base include salts with trimethylamine, triethylamine, pyridine, picoline, 2,6-lutidine, ethanolamine, diethanolamine, triethanolamine, cyclohexylamine, dicyclohexylamine and N,N'-dibenzylethylenediamine. Examples of the salt with an inorganic acid include salts with hydrochloric acid, boric acid, nitric acid, sulfuric acid and phosphoric acid. Examples of the salt with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid and p-toluenesulfonic acid. Examples of the salt with a basic amino acid include salts with arginine, lysine and ornithine. Examples of the salt with an acidic amino acid include salts with aspartic acid and glutamic acid. The list of suitable salts is disclosed in Remington's Pharmaceutical Sciences, 17th ed., Mack Publishing Company, Easton, Pa., p 1418, 1985, the entire disclosure of which is incorporated herein by reference.

In one embodiment of the invention, said peptide comprises from 6 to 20 amino acids and a phosphorylated $GpYX_1X_2X_1S$ motif (SEQ ID NO: 33), wherein each $X_1$ independently is M or Nle and $X_2$ is P, F or M.

In another embodiment of the invention, said peptide comprises from 6 to 20 amino acids and a phosphorylated $DpYX_1X_2X_1S$ motif (SEQ ID NO: 34), wherein each $X_1$ independently is M or Nle and $X_2$ is P or N.

In another embodiment of the invention, said peptide comprises from 6 to 20 amino acids and a phosphorylated $EpYX_1NX_1D$ motif (SEQ ID NO: 35), wherein each $X_1$ independently is M or Nle.

In another embodiment of the invention, said peptide comprises from 6 to 20 amino acids and a phosphorylated $DpYX_1TX_1Q$ motif (SEQ ID NO: 36), wherein each $X_1$ independently is M or Nle.

Another object of the invention is a peptide as described here above or a pharmaceutical composition as described here above for treating cancer or for use in treating cancer.

Another object of the invention is a method for treating cancer, comprising the administration to a subject in need thereof of a therapeutically effective amount of at least one of the peptides of the invention.

According to the invention, the subject may be any mammal, preferably a human. "Therapeutically effective dose or amount" refers to a dosage level sufficient to induce a desired biological result. That result can be alleviation of the signs, symptoms, or causes of a disease, or any other desired alteration of a biological system. Preferably, this dose or amount will be sufficient to alleviate the cancerous condition by killing the cancerous cells, but also to an effect that results in the inhibition of growth and/or metastasis of the cancer.

Cancers that may be treated by the peptides, compositions and methods of the invention include, but are not limited to:

Cardiac: sarcoma (angiosarcoma, fibrosarcoma, rhabdomyosarcoma, liposarcoma), myxoma, rhabdomyoma, fibroma, lipoma and teratoma;

Lung: non-small cell lung, bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatosis hamartoma, mesothelioma;

Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal;

Genitourinary tract: kidney (adenocarcinoma, Wihn's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver: hepatoma (hepatocellular carcinoma), cholangiocarcinoma, hepatoblastoma, angiosarcoma, hepatocellular adenoma, hemangioma;

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochondroma (osteocartilaginous exostoses), benign chondroma, chondroblastoma, chondromyxofibroma, osteoid osteoma and giant cell tumors;

Nervous system: skull (osteoma, hemangioma, granuloma, xanthoma, osteitis deformans), meninges (meningioma, meningosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granuEosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes [carcinoma]);

Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

Cancers that may be treated by the peptides, compositions and methods of the invention include, but are not limited to: breast, prostate, colon, colorectal, lung, non-small cell lung, brain, testicular, stomach, pancreas, skin, small intestine, large intestine, throat, head and neck, oral, bone, liver, bladder, kidney, thyroid and blood.

Cancers that may be treated by the peptides, compositions and methods of the invention include: breast, prostate, colon, ovarian, colorectal, lung and non-small cell lung.

Cancers that may be treated by the peptides, compositions and methods of the invention include: breast, colon (colorectal) and lung (non-small cell lung).

Cancers that may be treated by the peptides, compositions and methods of the invention include: lymphoma and leukemia.

Cancers that may be treated by the peptides, compositions and methods of the invention include angiogenesis-related cancers such as breast carcinoma, bladder carcinomas, colon carcinomas, oral cavity tumors, advanced tumors, hairy cell leukemia, melanoma, advanced head and neck, metastatic renal cell, non-Hodgkin's lymphoma, metastatic breast, breast adenocarcinoma, advanced melanoma, pancreatic, gastric, glioblastoma, lung, ovarian, non-small cell lung, prostate, small cell lung, renal cell carcinoma, various solid tumors, multiple myeloma, metastatic prostate, malignant glioma, renal cancer, lymphoma, refractory metastatic disease, refractory multiple myeloma, cervical cancer, Kaposi's sarcoma, recurrent anaplastic glioma, and metastatic colon cancer.

The peptides, compositions and methods of the invention are also intended to prevent or decrease tumor cell metastasis.

Further included within the scope of the invention is a method of treating or preventing a disease in which angiogenesis is implicated, comprising administering to a subject in need of such treatment a therapeutically effective amount of a peptide of the present invention.

Angiogenesis-related diseases include ocular neovascular diseases (such as, for example, ischemic retinopathy, diabetic retinopathy, retinopathy of prematurity, retinal vein occlusions, age-related macular degeneration, corneal neovascularisation, neovascular glaucoma), atherosclerosis, arthritis, psoriasis, obesity and Alzheimer's disease.

Further included within the scope of the invention is a method of treating or preventing hyperproliferative disorders such as restenosis, inflammation, autoimmune diseases and allergy/asthma, comprising administering to a subject in need of such treatment a therapeutically effective amount of a peptide of the present invention.

According to the invention, the peptides of the invention may be administered orally, topically, or by parenteral means, including subcutaneous, transdermal or intramuscular injection, implantation of sustained release depots, intravenous injection, intranasal administration, and the like.

In one embodiment of the invention, the peptide of the invention may be intraocularly administered. As used herein, "Intraocularly" means by intraocular route of administration. In one embodiment, the intraocular route of administration is an administration within the interior of the eye, preferably within the posterior segment of the eye, more preferably within the vitreous. Preferred intraocular route is intravitreal injection. As used herein, "Interior of the eye" means any area located within the eyeball, including the anterior and posterior segment of the eye, and which generally includes, but is not limited to, any functional (e.g., for vision) or structural tissues found within the eyeball, or tissues or cellular layers that partly or completely line the interior of the eyeball. Specific examples of areas include the anterior chamber, the posterior chamber, the vitreous cavity, the choroid, the macula, and the retina, and blood vessels and nerves which vascularize or innervate a posterior ocular region or site. According to a preferred embodiment, interior of the eye means the posterior segment of the eye, including the posterior chamber, the vitreous cavity, the choroid, the macula, and the retina, and blood vessels and nerves which vascularize or innervate a posterior ocular region or site.

In one embodiment of the invention, the peptide of the invention may be administered by topical ocular administration, such as, for example, the administration of eye drops or by bathing the eye in an ophthalmic solution comprising the peptide or the composition of the invention.

According to the invention, the compositions comprising the peptides of the invention may be aqueous solutions, emulsions, creams, ointments, suspensions, gels, liposomal suspensions, and the like.

According to the invention, the composition comprises the peptide of the invention in an amount of about 0.0001 to 500 mg of the peptide per milliliter or gram of the composition, preferably from about 0.001 to 50 mg, more preferably from 0.01 to 5 mg and even more preferably from 0.1 to 1 mg of the peptide per milliliter or gram of the composition.

According to the invention, the composition comprises the peptide of the invention in an amount from about 0.01% to 90% by weight to the volume of the total composition, preferably from 0.1 to 10% by weight, more preferably from 1 to 5% by weight to the volume of the total composition.

In another embodiment of the invention, the composition comprising at least one of the peptides of the invention may further comprise at least one cytotoxic, chemotherapeutic or anti-cancer agent.

In another embodiment of the invention, the composition comprising at least one of the peptides of the invention may be used in combination with at least one cytotoxic, chemotherapeutic or anti-cancer agent.

Examples of anti-cancer agents include, but are not limited to, alkylating agents or agents with an alkylating action, such as, for example, cyclophosphamide (CTX; e.g. CYTOXAN®), chlorambucil (CHL; e.g. LEUKERAN®), cisplatin (C is P; e.g. PLATINOL®), oxaliplatin (e.g. ELOXATIN™), busulfan (e.g. MYLERAN®), melphalan, carmustine (BCNU), streptozotocin, triethylenemelamine (TEM), mitomycin C, and the like; anti-metabolites, such as, for example, methotrexate (MTX), etoposide (VP16; e.g. VEPESID®), 6-mercaptopurine (6 MP), 6-thioguanine (6TG), cytarabine (Ara-C), 5-fluorouracil (5-FU), capecitabine (e.g. XELODA®), dacarbazine (DTIC), and the like; antibiotics, such as, for example, actinomycin D, doxorubicin (DXR; e.g. ADRIAMYCIN®), daunorubicin (daunomycin), bleomycin, mithramycin and the like; alkaloids, such as, for example, vinca alkaloids such as, for example, vincristine (VCR), vinblastine, and the like; and other antitumor agents, such as, for example, paclitaxel (e.g. TAXOL®) and paclitaxel derivatives, the cytostatic agents, glucocorticoids such as dexamethasone (DEX; e.g. DECADRON®) and corticosteroids such as, for example, prednisone, nucleoside enzyme inhibitors such as, for example, hydroxyurea, amino acid depleting enzymes such as, for example, asparaginase, leucovorin, folinic acid, raltitrexed, and other folic acid derivatives, and similar, diverse antitumor agents. The following agents may also be used as additional agents: amifostine (e.g. ETHYOL®), dactinomycin, mechlorethamine (nitrogen mustard), streptozocin, cyclophosphamide, lornustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, cladribine, camptothecin, 10-hydroxy 7-ethyl-camptothecin (SN38), floxuridine, fludarabine, ifosfamide, idarubicin, mesna, interferon alpha, interferon beta, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, or chlorambucil.

The use of the cytotoxic, chemotherapeutic and other anticancer agents described above in chemotherapeutic regimens is generally well characterized in the cancer therapy arts, and their use herein falls under the same considerations for monitoring tolerance and effectiveness and for controlling administration routes and dosages, with some adjustments. Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

This invention will be better understood from the Experimental Details that follow. However, one skilled in the art will readily appreciate that the specific methods and results discussed are merely illustrative of the invention as described more fully in the claims which follow thereafter, and are not to be considered in any way as limited thereto.

EXAMPLES

Example 1

Materials and Methods

Materials

Figure 1:
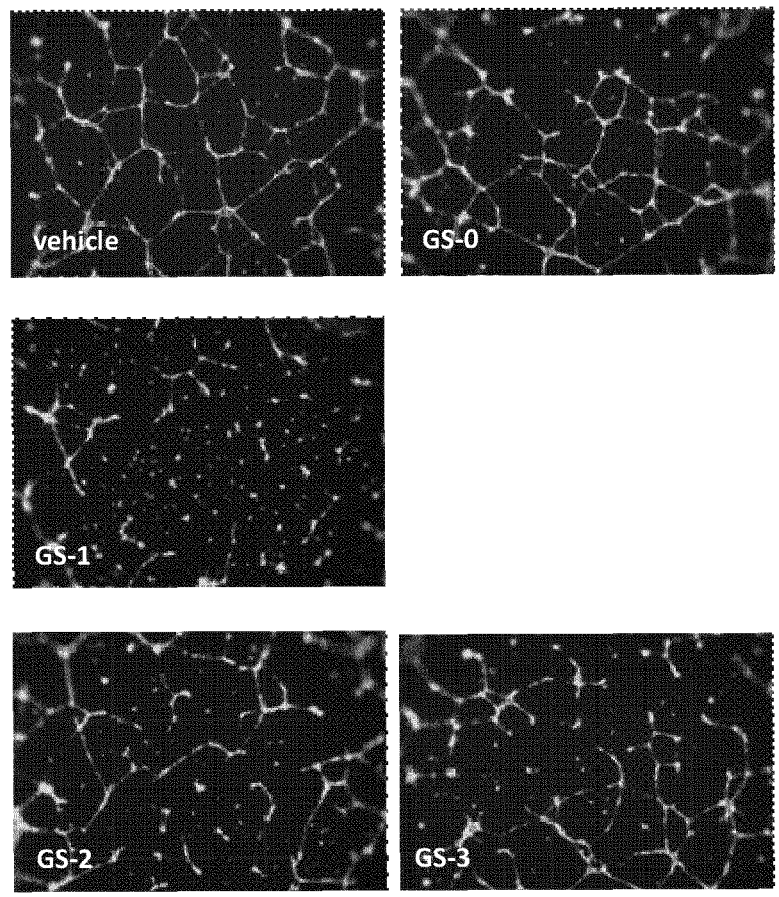
FIG. 1: Representative images of the in vitro angiogenesis assay (images were taken at 18 h post incubation).

The culture medium EGM-2MV was from Lonza (Verviers, Belgium). Calcium- and Magnesium-free PBS, trypsine-EDTA (Versene), were purchased from Eurobio (Les Ulis, France). Matrigel was purchased from Becton Dickinson (Le Pont de Claix, France). Bacterial culture medium LB, Thermoscript and the high fidelity Platinum HIFI enzymes were obtained from Invitrogen (Cergy Pontoise, France). Rneasy mini kit, Qiaquick and Qiaprep miniprep were obtained from Qiagen (Courtaboeuf, France), from Roche Applied Science. Peptides were chemically synthesized by GeneCust with N-terminal acetylation and C-terminal amidation as chemical modifications. All peptides were subjected to HPLC-purification step and furnished as lyophilized powder with at least 95% of purity.

Methods

Angiogenesis Assay

Angiogenesis of human microvascular endothelial cells (HMEC) was induced in vitro using a Matrigel assay described by Al-Mahmood et al (2009, JPET, 2009; 58:933). This method is based on the differentiation of endothelial cells to form capillary structures on a Matrigel Matrix. Matrigel is prepared the Engelbreth-Holm-Swarm (EHS) mouse tumor, which represents a complex mixture of basement membrane proteins including type IV collagen, entactin, proteo-heparan sulfate and other growth factors.

Briefly, 250 µl of Matrigel were transferred to each well of a 24-well culture plate and incubated at 37° C. for 30 min to allow for the matrix solution to solidify. HMEC grown in complete growth medium EGM-2MV were harvested by trypsin, suspended in the same growth medium and 500 µl containing 70 000 cells were added on top of the solidified Matrigel in each well and in the presence or absence of peptide. Cells were maintained in a humidified atmosphere air containing 5% $CO_2$ at 37° C. for 18-24 hrs. Endothelial tube formation was observed and photographed under an inverted light microscope.

Proliferation Assay

Five thousand HMEC (5 000 cells/ml of growth medium) were seeded in 96-well cell culture grade micro-plates (100 µl/well) and incubated with the indicated peptide at the indicated final concentrations for 42 hrs at 37° C., cells proliferation was measured using thiazolyl blue tetrazolium bromide (MTT) method. Briefly, MTT (Sigma) was dissolved in PBS at 5 mg/ml, the solution was filtered (0.22 µm) and 10 µl were added to each well of the 96-well micro-plates. After 3 hrs of incubation at 37° C., 5% $CO_2$ humidified atmosphere, the micro-plates were centrifuged at 220×g for 10 min, the supernatant was discarded, and the crystals dissolved by the addition of 100 µl of DMSO to each well. The optical density (OD) at 570 nm was then measured using µQuant micro-plate reader coupled to the KC4 (Bio-Tek, Colmar France) software. The OD was corrected by subtracting blank-well OD values (the OD values obtained from wells without cells), and the inhibition of cell proliferation was measured relative to control (OD obtained from wells with untreated HUVEC representing the maximal proliferative response, i.e. 100%).

Protein Quantification

Serum-deprived HMEC were incubated with different concentrations of peptides for 24 h at 37° C. under 5% $CO_2$ for 6 h. After 3 washes with ice-cold PBS, cells were suspended with the protein extraction buffer (PEB) (20 mM Tris-HCl pH 7.5, 150 mM NaCl, 1 mM EDTA, 1 mM EGTA, 1% Triton, 25 mM sodium pyrophosphate, 1 mM β-glycero-phosphate, 1 mM $Na_3Vo_4$, 1 µg/ml leupeptine, 1 µM PMSF). The protein content was measured by Bradford.

Cell Treatment and Immunoprecipitation

Human EC grown in EGM-2MV (80% confluence) were incubated with the peptides of the invention or vehicle for the indicated time, washed three times in cold PBS and directly lysed in 2 ml of ice-cold lysis buffer (10 mM Tris pH 7.5, 150 mM NaCl, 1 mM PMSF, 0.5 µg/ml leupeptin, 1 µg/ml pepstatin A, and 1 µg/ml aprotinin) by incubation for 30 min at 4° C. Cell lysate were spun at 104 g for 10 min, insoluble materials were discarded, and protein contents measured by Bradford assay of supernatants were adjusted. Cell lysate (1 ml) was precleared with 25 µl of protein G-plus agarose beads (Santa Cruz) for 30 min, and proteins were then immunoprecipitated by adding 2 µg of the indicated antibody and incubated for 1 hr. The immunocomplex was pulled down with protein G-plus agarose beads and the beads were washed three times with lysis buffer. The immunoprecipitates were separated by NuPAGE® 4-12% Bis-Tris gel electrophoresis under reducing conditions, transferred to PVDF membrane (Novex System, Invitrogen), and the membrane was blocked with 5% (w/v) non-fat milk in TBS containing 0.1% v/v Tween-20 for 1 hr. The membrane was incubated with the indicated primary antibody for 2 hr, washed three times, and incubated with the appropriate HRP-conjugated secondary antibody and revealed by enhanced chemiluminescence, ECL plus (GE Healthcare, Velizy, France).

Results

The following peptides were tested:

```
GpYMFMS              GS-1        (SEQ ID NO: 37)

EpYMNMD              GS-2        (SEQ ID NO: 38)

DpYMTMQ              GS-3        (SEQ ID NO: 39)

NYICMG               GS-0        (SEQ ID NO: 40)
(tyrosine non phosphorylated
peptide used as control).
```

Influence of the Peptides Having a Phosphorylated $pYX_1X_2X_1$ Motif According to the Invention onto In Vitro Angiogenesis The designed tyrosine phosphorylated and non phosphorylated peptides were tested for their influence onto the in vitro angiogenesis. The results of the in vitro angiogenesis assay were presented in FIG. 1, using HMEC and 500 µg/ml final concentration of each peptide. These results show that the tyrosine non phosphorylated peptide GS-0 used as control have not and/or negligible in vitro angiogenesis-inhibitory activity (FIG. 1). Results presented in the same figure showed also that the tyrosine phosphorylated small peptide GS-1, GS-2, and GS-3 have in vitro angiogenesis-inhibitory activities.

Influence of the Peptides onto Association of p85 to IRS-1

As it is widely admitted that the tyrosine phosphorylation of IRS-1 leads to its association with the regulatory subunit (p85) of the enzyme PI-3K, and this event lead to important increases in the enzymatic activity of this later, we have investigated the influence of the tyrosine phosphorylated and non phosphorylated peptides onto the recruitment of the regulatory subunit (p85) of the enzyme PI-3K by IRS-1. For that, human microvascular endothelial cells (HMEC) were incubated with the tyrosine phosphorylated and non phosphorylated peptides (final concentration of peptide 500 µg/ml) followed by cells lysis and immuoprecipitation of the protein IRS-1. The immunoprecipitates were then resolved in SDS-PAGE, proteins were transferred to membranes, and the membranes were immunoblotted with an anti-p85 PI3K monoclonal antibody.

Figure 2:
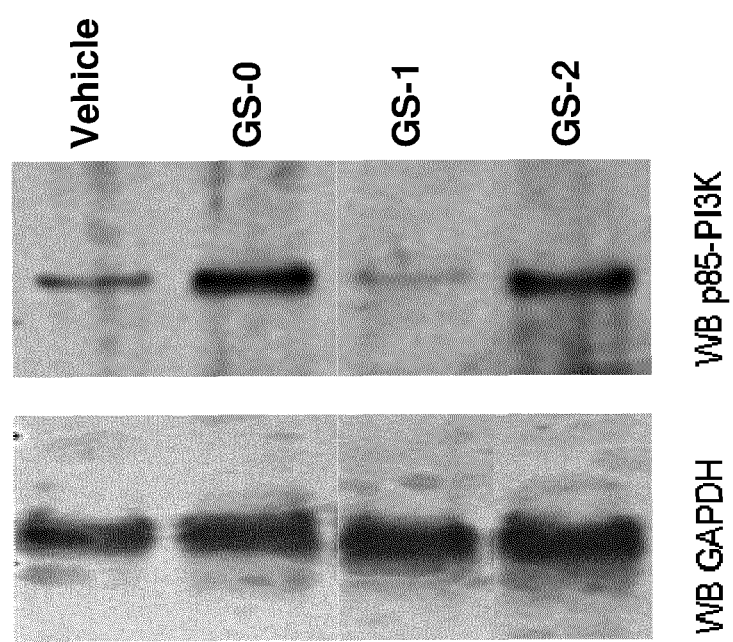
FIG. 2: Influence of the tyrosine phosphorylated and non phosphorylated peptides onto the recruitment of the regulatory subunit (p85) of the enzyme PI-3K by IRS-1

Results presented in FIG. 2 show that the tyrosine non phosphorylated peptide GS-0 used as control has no and/or negligible influence onto the recruitment of the regulatory subunit (p85) of the enzyme PI3K by IRS-1. Results presented in the same figure show also that the tyrosine phosphorylated peptide GS-2 has moderate inhibitory effects onto the recruitment of the regulatory subunit (p85) of the enzyme PI3K by IRS-1 and the tyrosine phosphorylated peptide GS-1 a very strong inhibitory effects onto the recruitment of the regulatory subunit (p85) of the enzyme PI-3K by IRS-1.

Influence of the Peptides onto mTOR in HMEC

Figure 3:
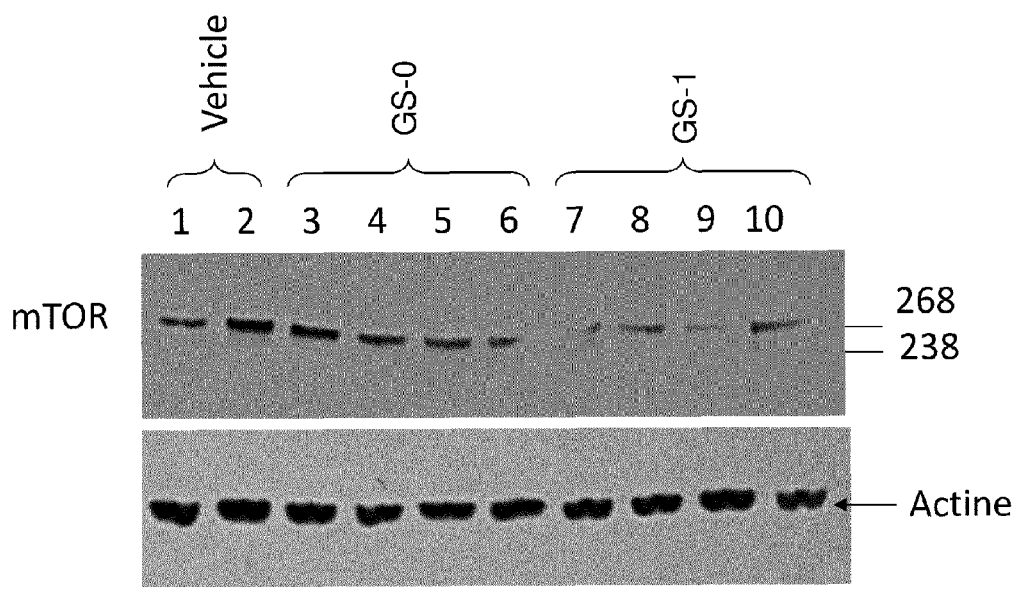
FIG. 3: (A) Influence of GS-0 and GS-1 onto the activation of mTor. (B) Influence of GS-0 and GS-2 onto the activation of mTor.
Figure 3:
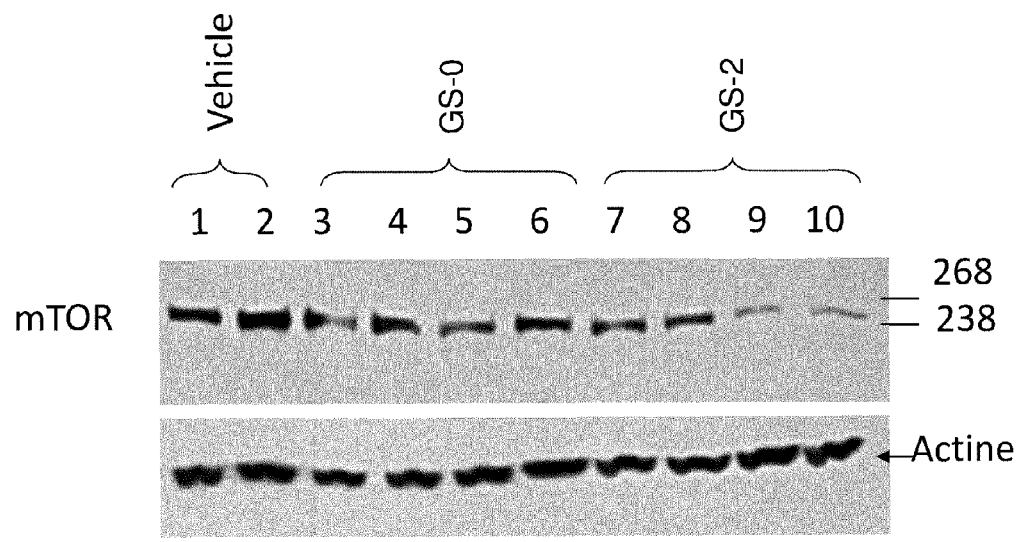

The status of mTOR in the HMEC following incubation with peptides GS-0 and GS-1 was investigated. Results showed that HMEC (Vehicle) posses an important level of mTOR (FIGS. 3A and B, anti-mTor antibody, Ozyme, 2971 (Ser2448)). HMEC cell lines incubated with peptide GS-0 have equivalent amounts of mTOR as cell incubated with vehicle. In contrast, HMEC cell line incubated with either GS-1 or GS-2 has much less amounts of mTOR relative to the HMEC incubated with vehicle or with GS-0, indicating that the peptide GS-1 inhibits mTOR activation.

Example 2

Methods

Cell Culture:

H460 cell line has cytology compatible with human Non-Small Cell Lung Cancer (NSCL). Cells were grown in MEM medium containing 10% FCS at 37° C., 5% $CO_2$ humidified atmosphere. The absence of mycoplasms was confirmed by using the PCR Mycoplasma Detection kit (Takara).

Tumor Xenografts in Nude Mice and Treatments:

All experiments were reviewed by the Genopole's institutional animal care and use committee and were performed in accordance with institutional guidelines for animal care. Female BALB/c nu/nu mice (n=30) were used at 5-6 weeks of age. The animals were housed in laminar air-flow cabinets under pathogen-free conditions with a 12 h light/12 h dark schedule, and fed autoclaved standard chow and water ad libitum. The NCI-H460 human NSCL cell line was obtained from American Type Culture Collection (ATCC) and cells were grown in RPMI medium 1640 supplemented with 1 µM sodium pyruvate. Tumor cells ($10^7$ cells in 200 µl of HBSS) were injected subcutaneously into the right flanks of mice. After engraftment, tumor volume was measured by Vernier callipers, and calculated as described in Balsari A et al. (Balsari A et al. (2004) Eur J Cancer 40: 1275-1281). At tumor volume about 150 mm3, animals were randomized, and separated into five groups of five animals. Control mice (group 1) were intraperitoneally injected with vehicle (10% DMSO in buffer saline) every day. GS-0 was dissolved in vehicle and intraperitoneally injected (group 2) every day (12 injections). GS-1 was dissolved in vehicle and intraperitoneally injected (group 3) every day (12 injections). Tumor volume and body weight were measured every other day over the treatment period (12 days).

Preparation of Peptides and Dilutions

GS-1 as well as the control peptide GS-0 were solubilized in DMSO and the resulting solutions were diluted 10 times with phosphate buffer saline (PBS) to obtain a concentration of 1 mg of peptide/ml of 10% DMSO in PBS. At this concentration, all peptides were soluble in 10% DMSO.

Results

Mean Body Weight of Mice Bearing NCI-H40 and Toxicity Issues

The results of body weight monitoring and toxicity are shown in Table 1. The vehicle had no impact: mouse behavior and body weight gain were normal and no animal died prematurely. No toxicity and no body weight loss were observed during the course of the treatment with the test substances GS-0 and GS-1 at the doses of 8 mg/kg.

TABLE 1

Mean body weight of mice bearing NCI-H40 tumors treated with the vehicle, GS-0 at 8 mg/kg and GS-1 at 8 mg/kg

|  | D1 | D3 | D5 | D7 | D9 | D11 | D13 |
|---|---|---|---|---|---|---|---|
| Vehicle | 22.89 | 24.15 | 24.14 | 24.30 | 24.54 | 23.89 | 24.77 |
|  | ± | ± | ± | ± | ± | ± | ± |
|  | 0.30 | 0.92 | 0.74 | 1.12 | 1.11 | 0.70 | 1.07 |
| GS-0 | 20.91 | 21.37 | 21.65 | 21.81 | 22.52 | 22.76 | 22.36 |
|  | ± | ± | ± | ± | ± | ± | ± |
|  | 5.09 | 5.14 | 5.60 | 5.47 | 5.17 | 5.37 | 5.84 |
| GS-1 | 23.58 | 23.27 | 20.69 | 23.29 | 23.72 | 23.81 | 23.48 |
|  | ± | ± | ± | ± | ± | ± | ± |
|  | 2.06 | 1.79 | 2.87 | 1.78 | 1.42 | 1.77 | 1.57 |

In Vivo Tumor Growth

Figure 4:
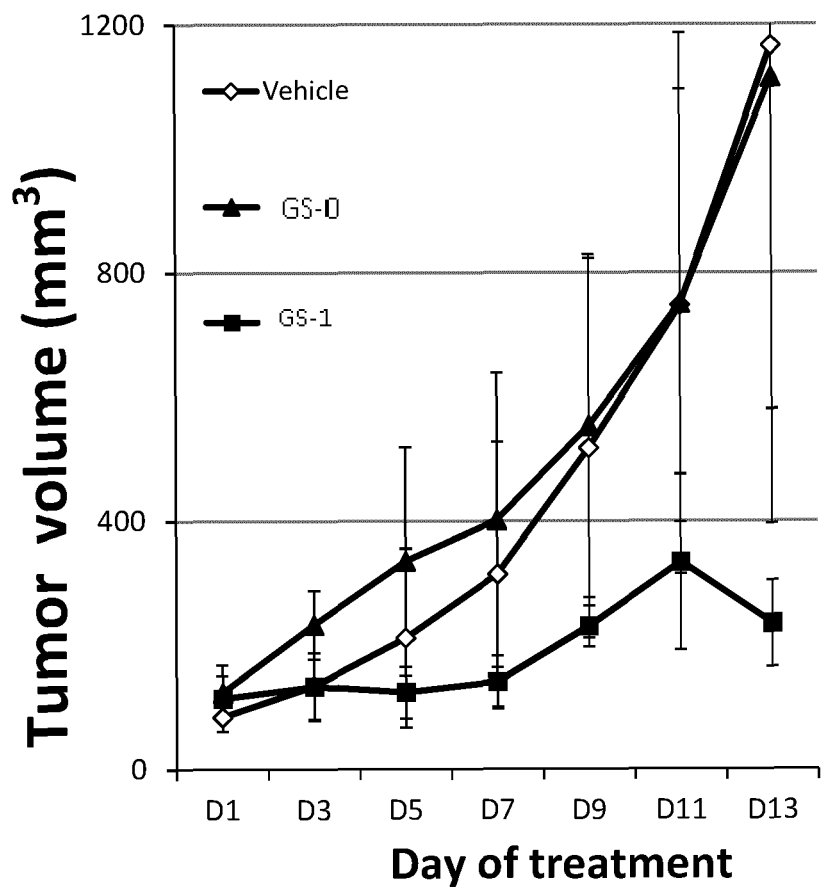
FIG. 4: Mean Tumor Volume curve of mice bearing NCI-H460 tumors treated with the vehicle, GS-0 at 8 mg/kg or GS-1 at 8 mg/kg.

The results of mean tumor volume are shown in FIG. 4 and Table 2. The evolution of the mean tumor volume with time for mice treated with vehicle, GS-0 and GS-1 showed that there were not statistically significant differences between the three groups of animals throughout the treatment period (12 days). At the end of treatment, the mean tumor volume of vehicle and GS-0 treated groups are 1165.64+769.22 (n=5); and 1114.83+534.50 (n=5) $mm^3$ respectively which are statistically not different from each other (p>0.05), indicating that the peptide GS-0 has no significant influence (p>0.05) on the in vivo growth of the tumor NCI-H460.

The evolution of the mean tumor volume with time show also that mice treated with GS-1 have a mean tumor volume statistically different from mice treated with vehicle, and GS-0 throughout the treatment period (12 days) (FIG. 4 and Table 2). A massive reduction of the mean tumor volume was observed in animals from group treated with GS-1 (234.98+69.22 $mm^3$; n=5) compared to group 1, the vehicle treated animals (1165.64+769.22 $mm^3$; n=5). The difference between the vehicle treated group and the GS-1 treated group treated reach the statistical significance (p=0.0004). The difference between the group treated with GS-1 (234.98+69.22 $mm^3$; n=5) and the groups treated with GS-0 (1114.83+534.50 $mm^3$; n=5) is also statistically different (p<0.05), indicating that the peptide GS-1 have highly significant and potent influence (p=0.0004) on the in vivo growth of the tumor NCI-H460. Indeed, the appreciation of the potent in vivo antitumor activity of the peptide GS-1 indicate that daily injection of GS-1 at 8 mg/kg for 12 successive days leads to about 80% inhibition of the in vivo tumor growth.

TABLE 2

Mean tumor volume of mice bearing NCI-H460 tumors treated with the vehicle, GS-0 at 8 mg/kg and GS-1 at 8 mg/kg. Results were expressed as mean body weight (g) + standard deviation.

|  | D1 | D3 | D5 | D7 | D9 | D11 | D13 |
|---|---|---|---|---|---|---|---|
| Vehicle | 83.92 | 133.99 | 211.47 | 313.92 | 517.51 | 747.16 | 1165.64 |
|  | ± | ± | ± | ± | ± | ± | ± |
|  | 22.28 | 53.69 | 144.12 | 213.31 | 305.71 | 348.36 | 769.22 |
| GS-0 | 123.48 | 232.87 | 335.13 | 401.53 | 552.95 | 750.63 | 1114.83 |
|  | ± | ± | ± | ± | ± | ± | ± |
|  | 44.68 | 54.82 | 184.14 | 236.93 | 276.69 | 435.84 | 534.50 |
| GS-1 | 113.99 | 133.11 | 123.77 | 140.52 | 230.54 | 333.54 | 234.98 |
|  | ± | ± | ± | ± | ± | ± | ± |
|  | 36.55 | 54.63 | 41.65 | 42.78 | 32.91 | 141.61 | 69.22 |

In conclusion, the peptide GS-1 shows a statistically significant and potent anti-tumoral activity against NCI-H460 in vivo.

Example 3

Methods

Cell Culture:

H460 cell line has cytology compatible with human Non-Small Cell Lung Cancer (NSCL). Cells were grown in MEM medium containing 10% FCS at 37° C., 5% $CO_2$ humidified atmosphere. The absence of mycoplasms was confirmed by using the PCR Mycoplasma Detection kit (Takara).

Tumor Xenografts in Nude Mice and Treatments:

All experiments were reviewed by the Genopole's institutional animal care and use committee and were performed in accordance with institutional guidelines for animal care. Female BALB/c nu/nu mice (n=30) were used at 5-6 weeks of age. The animals were housed in laminar air-flow cabinets under pathogen-free conditions with a 12 h light/12 h dark schedule, and fed autoclaved standard chow and water ad libitum. The NCI-H460 human NSCL cell line was obtained from American Type Culture Collection (ATCC) were grown in RPMI medium 1640 supplemented with 1 μM sodium pyruvate. Tumor cells ($10^7$ cells in 200 μl of HBSS) were injected subcutaneously into the right flanks of mice. After engraftment, tumor volume was measured by Vernier callipers, and calculated as described in Balsam A et al. (Balsari A et al. (2004) Eur J Cancer 40: 1275-1281). At tumor volume about 150 $mm^3$, animals were randomized, and separated into five groups of five animals. Control mice (group 1) were intraperitoneally injected with vehicle (10% DMSO in buffer saline) every day. GS-0 was dissolved in vehicle and intraperitoneally injected (group 2) every day (12 injections). GS-2 was dissolved in vehicle and intraperitoneally injected (group 3) every day (12 injections). Tumor volume and body weight were measured every other day over the treatment period (12 days).

Preparation of Peptides and Dilutions

GS-2 as well as the control peptide GS-0 were solubilized in DMSO and the resulting solutions were diluted 10 times with phosphate buffer saline (PBS) to obtain a concentration of 1 mg of peptide/ml of 10% DMSO in PBS. At this concentration, all peptides were soluble in 10% DMSO.

Results

Mean Body Weight of Mice Bearing NCI-H40 and Toxicity Issues

The results of body weight monitoring and toxicity are shown in Table 3. The vehicle had no impact: mouse behavior and body weight gain were normal and no animal died prematurely. No toxicity and no body weight loss were observed during the course of the treatment with the test substances GS-0 and GS-2 at the doses of 8 mg/kg.

TABLE 3

Mean body weight of mice bearing NCI-H40 tumors treated with the vehicle, GS-0 at 8 mg/kg and GS-2 at 8 mg/kg

|  | D1 | D3 | D5 | D7 | D9 | D11 | D13 |
|---|---|---|---|---|---|---|---|
| Vehicle | 22.89 | 24.15 | 24.14 | 24.30 | 24.54 | 23.89 | 24.77 |
|  | ± | ± | ± | ± | ± | ± | ± |
|  | 0.30 | 0.92 | 0.74 | 1.12 | 1.11 | 0.70 | 1.07 |
| GS-0 | 20.91 | 21.37 | 21.65 | 21.81 | 22.52 | 22.76 | 22.36 |
|  | ± | ± | ± | ± | ± | ± | ± |
|  | 5.09 | 5.14 | 5.60 | 5.47 | 5.17 | 5.37 | 5.84 |
| GS-2 | 22.59 | 22.32 | 22.78 | 23.10 | 23.00 | 23.51 | 23.05 |
|  | + | ± | ± | ± | ± | ± | ± |
|  | 2.33 | 1.52 | 1.02 | 1.12 | 1.14 | 0.94 | 0.80 |

In Vivo Tumor Growth

Figure 5:
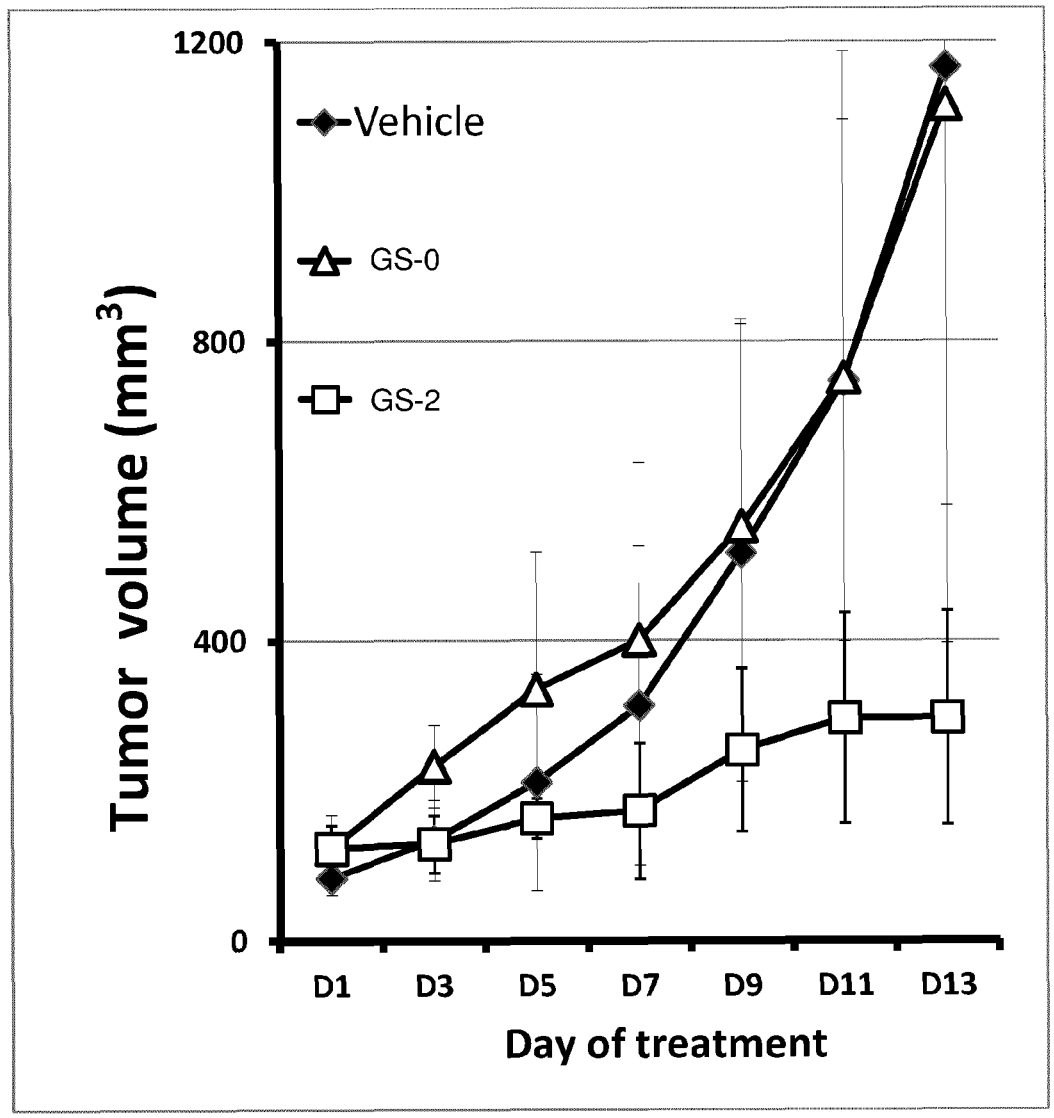
FIG. 5: Mean Tumor Volume curve of mice bearing NCI-H460 tumors treated with the vehicle, GS-0 at 8 mg/kg or GS-2 at 8 mg/kg.

The results of mean tumor volume are shown in FIG. 5 and Table 4. The evolution of the mean tumor volume with time for mice treated with vehicle, GS-0 and GS-2 showed that there were not statistically significant differences between the three groups of animals throughout the treatment period (12 days). At the end of treatment, the mean tumor volume of vehicle and GS-0 treated groups are 1165.64+769.22 (n=5); and 1114.83+534.50 (n=5) mm$^3$ respectively which are statistically not different from each other (p>0.05), indicating that the peptide GS-0 has no significant influence (p>0.05) on the in vivo growth of the tumor NCI-H460.

The evolution of the mean tumor volume with time show also that mice treated with GS-2 have a mean tumor volume statistically different from mice treated with vehicle, and GS-0 throughout the treatment period (12 days) (FIG. 4 and Table 2). A massive reduction of the mean tumor volume was observed in animals from group treated with GS-2 (297.28+142.67 mm$^3$; n=5) compared to group 1, the vehicle treated animals (1165.64+769.22 mm$^3$; n=5). The difference between the vehicle treated group and the GS-1 treated group treated reach the statistical significance (p=0.0065). The difference between the group treated with GS-2 (297.28+142.67 mm$^3$; n=5) and the groups treated with GS-0 (1114.83+534.50 mm$^3$; n=5) is also statistically different (p<0.05), indicating that the peptide GS-2 has highly significant and potent influence (p=0.0065) on the in vivo growth of the tumor NCI-H460. Indeed, the appreciation of the potent in vivo antitumor activity of the peptide GS-1 indicate that daily injection of GS-2 at 8 mg/kg for 12 successive days leads to about 80% inhibition of the in vivo tumor growth.

TABLE 4

Mean tumor volume of mice bearing NCI-H460 tumors treated with the vehicle, GS-0 at 8 mg/kg and GS-2 at 8 mg/kg. Results were expressed as mean body weight (g) + standard deviation.

|  | D1 | D3 | D5 | D7 | D9 | D11 | D13 |
|---|---|---|---|---|---|---|---|
| Vehicle | 83.92 | 133.99 | 211.47 | 313.92 | 517.51 | 747.16 | 1165.64 |
|  | ± | ± | ± | ± | ± | ± | ± |
|  | 22.28 | 53.69 | 144.12 | 213.31 | 305.71 | 348.36 | 769.22 |
| GS-0 | 123.48 | 232.87 | 335.13 | 401.53 | 552.95 | 750.63 | 1114.83 |
|  | ± | ± | ± | ± | ± | ± | ± |
|  | 44.68 | 54.82 | 184.14 | 236.93 | 276.69 | 435.84 | 534.50 |
| GS-2 | 123.81 | 129.20 | 163.14 | 173.53 | 254.50 | 296.74 | 297.28 |
|  | + | + | + | + | + | + | + |
|  | 30.35 | 38.16 | 26.43 | 90.54 | 109.00 | 140.78 | 142.67 |

In conclusion, the peptide GS-2 shows a statistically significant and potent anti-tumoral activity against NCI-H460 in vivo.

The invention claimed is:

1. A method of treating ocular neovascular diseases, treating angiogenesis-related cancers and/or tumors, and/or for inhibiting cancer metastasis in a subject comprising:
   obtaining a therapeutically sufficient amount of a peptide from 4 to 50 amino acids in length comprising a phosphorylated $pYX_1FX_1$ motif, wherein each $X_1$ independently is M or Nle; and
   administering the amount of peptide to the subject.

2. The method of claim 1, further comprising administering at least one cytotoxic, chemotherapeutic, or anti-cancer agent to the subject.

3. The method of claim 1, wherein the peptide is from 6 to 20 amino acids in length and comprises a phosphorylated $GpYX_1FX_1S$ motif (SEQ ID NO: 15), wherein each $X_1$ independently is M or Nle.

4. A method of inhibiting cancer metastasis in a subject comprising:
   obtaining a therapeutically sufficient amount of a peptide from 4 to 50 amino acids in length comprising a phosphorylated $pYX_1FX_1$ motif, wherein each $X_1$ independently is M or Nle; and
   administering the amount of peptide to the subject.

5. A method of inhibiting cancer angiogenesis in a subject comprising:
   obtaining a therapeutically sufficient amount of a peptide from 4 to 50 amino acids in length comprising a phosphorylated $pYX_1FX_1$ motif, wherein each $X_1$ independently is M or Nle; and
   administering the amount of peptide to the subject.

* * * * *

SEQUENCE LISTING

```
<160> NUMBER OF SEQ ID NOS: 64

<210> SEQ ID NO 1
<211> LENGTH: 4
<212> TYPE: PRT
<213> ORGANISM: Artificial Sequence
<220> FEATURE:
<221> NAME/KEY: SOURCE
<222> LOCATION: 1..4
<223> OTHER INFORMATION: /mol_type="protein"
      /note="YX1X2X1 motif"
      /organism="Artificial Sequence"
<220> FEATURE:
<221> NAME/KEY: MOD_RES
<222> LOCATION: 1..1
<223> OTHER INFORMATION: PHOSPHORYLATION
<220> FEATURE:
<221> NAME/KEY: SITE
<222> LOCATION: 2..2
<223> OTHER INFORMATION: X is M or Nle
<220> FEATURE:
<221> NAME/KEY: SITE
<222> LOCATION: 3..3
<223> OTHER INFORMATION: X is any amino acids
<220> FEATURE:
```

```
<221> NAME/KEY: SITE
<222> LOCATION: 4..4
<223> OTHER INFORMATION: X is M or Nle

<400> SEQUENCE: 1

Tyr Xaa Xaa Xaa
1

<210> SEQ ID NO 2
<211> LENGTH: 11
<212> TYPE: PRT
<213> ORGANISM: Artificial Sequence
<220> FEATURE:
<221> NAME/KEY: SOURCE
<222> LOCATION: 1..11
<223> OTHER INFORMATION: /mol_type="protein"
      /note="peptide"
      /organism="Artificial Sequence"
<220> FEATURE:
<221> NAME/KEY: MOD_RES
<222> LOCATION: 4..4
<223> OTHER INFORMATION: PHOSPHORYLATION

<400> SEQUENCE: 2

Asp Asp Gly Tyr Met Pro Met Ser Pro Gly Val
1               5                   10

<210> SEQ ID NO 3
<211> LENGTH: 11
<212> TYPE: PRT
<213> ORGANISM: Artificial Sequence
<220> FEATURE:
<221> NAME/KEY: SOURCE
<222> LOCATION: 1..11
<223> OTHER INFORMATION: /mol_type="protein"
      /note="peptide"
      /organism="Artificial Sequence"
<220> FEATURE:
<221> NAME/KEY: MOD_RES
<222> LOCATION: 4..4
<223> OTHER INFORMATION: PHOSPHORYLATION

<400> SEQUENCE: 3

Asn Gly Asp Tyr Met Pro Met Ser Pro Gly Val
1               5                   10

<210> SEQ ID NO 4
<211> LENGTH: 11
<212> TYPE: PRT
<213> ORGANISM: Artificial Sequencel
<220> FEATURE:
<221> NAME/KEY: SOURCE
<222> LOCATION: 1..11
<223> OTHER INFORMATION: /mol_type="protein"
      /note="peptide"
      /organism="Artificial Sequencel"
<220> FEATURE:
<221> NAME/KEY: MOD_RES
<222> LOCATION: 4..4
<223> OTHER INFORMATION: PHOSPHORYLATION

<400> SEQUENCE: 4

Pro Asn Gly Tyr Met Met Met Ser Pro Ser Gly
1               5                   10

<210> SEQ ID NO 5
<211> LENGTH: 11
<212> TYPE: PRT
<213> ORGANISM: Artificial Sequence
<220> FEATURE:
<221> NAME/KEY: SOURCE
```

```
<222> LOCATION: 1..11
<223> OTHER INFORMATION: /mol_type="protein"
      /note="peptide"
      /organism="Artificial Sequence"
<220> FEATURE:
<221> NAME/KEY: MOD_RES
<222> LOCATION: 4..4
<223> OTHER INFORMATION: PHOSPHORYLATION

<400> SEQUENCE: 5

Thr Gly Asp Tyr Met Asn Met Ser Pro Val Gly
1               5                   10

<210> SEQ ID NO 6
<211> LENGTH: 11
<212> TYPE: PRT
<213> ORGANISM: Artificial Sequence
<220> FEATURE:
<221> NAME/KEY: SOURCE
<222> LOCATION: 1..11
<223> OTHER INFORMATION: /mol_type="protein"
      /note="peptide"
      /organism="Artificial Sequence"
<220> FEATURE:
<221> NAME/KEY: MOD_RES
<222> LOCATION: 4..4
<223> OTHER INFORMATION: PHOSPHORYLATION

<400> SEQUENCE: 6

Ser Glu Glu Tyr Met Asn Met Asp Leu Gly Pro
1               5                   10

<210> SEQ ID NO 7
<211> LENGTH: 16
<212> TYPE: PRT
<213> ORGANISM: Artificial Sequence
<220> FEATURE:
<221> NAME/KEY: SOURCE
<222> LOCATION: 1..16
<223> OTHER INFORMATION: /mol_type="protein"
      /note="peptide"
      /organism="Artificial Sequence"
<220> FEATURE:
<221> NAME/KEY: MOD_RES
<222> LOCATION: 8..8
<223> OTHER INFORMATION: PHOSPHORYLATION

<400> SEQUENCE: 7

Lys Lys His Thr Asp Asp Gly Tyr Met Pro Met Ser Pro Gly Val Ala
1               5                   10                  15

<210> SEQ ID NO 8
<211> LENGTH: 16
<212> TYPE: PRT
<213> ORGANISM: Artificial Sequence
<220> FEATURE:
<221> NAME/KEY: SOURCE
<222> LOCATION: 1..16
<223> OTHER INFORMATION: /mol_type="protein"
      /note="peptide"
      /organism="Artificial Sequence"
<220> FEATURE:
<221> NAME/KEY: MOD_RES
<222> LOCATION: 8..8
<223> OTHER INFORMATION: PHOSPHORYLATION

<400> SEQUENCE: 8

Arg Lys Gly Asn Gly Asp Gly Tyr Met Pro Met Ser Pro Lys Ser Val
1               5                   10                  15

<210> SEQ ID NO 9
```

```
<211> LENGTH: 17
<212> TYPE: PRT
<213> ORGANISM: Artificial Sequence
<220> FEATURE:
<221> NAME/KEY: SOURCE
<222> LOCATION: 1..17
<223> OTHER INFORMATION: /mol_type="protein"
      /note="peptide"
      /organism="Artificial Sequence"
<220> FEATURE:
<221> NAME/KEY: MOD_RES
<222> LOCATION: 9..9
<223> OTHER INFORMATION: PHOSPHORYLATION

<400> SEQUENCE: 9

Lys Lys Arg Val Asp Pro Asn Gly Tyr Met Met Met Ser Pro Ser Gly
1               5                   10                  15

Ser

<210> SEQ ID NO 10
<211> LENGTH: 18
<212> TYPE: PRT
<213> ORGANISM: Artificial Sequence
<220> FEATURE:
<221> NAME/KEY: SOURCE
<222> LOCATION: 1..18
<223> OTHER INFORMATION: /mol_type="protein"
      /note="peptide"
      /organism="Artificial Sequence"
<220> FEATURE:
<221> NAME/KEY: MOD_RES
<222> LOCATION: 10..10
<223> OTHER INFORMATION: PHOSPHORYLATION

<400> SEQUENCE: 10

Lys Lys Lys Leu Pro Ala Thr Gly Asp Tyr Met Asn Met Ser Pro Val
1               5                   10                  15

Gly Asp

<210> SEQ ID NO 11
<211> LENGTH: 16
<212> TYPE: PRT
<213> ORGANISM: Artificial Sequence
<220> FEATURE:
<221> NAME/KEY: SOURCE
<222> LOCATION: 1..16
<223> OTHER INFORMATION: /mol_type="protein"
      /note="peptide"
      /organism="Artificial Sequence"
<220> FEATURE:
<221> NAME/KEY: MOD_RES
<222> LOCATION: 7..7
<223> OTHER INFORMATION: PHOSPHORYLATION

<400> SEQUENCE: 11

Lys Lys Gly Ser Glu Glu Tyr Met Asn Met Asp Leu Gly Pro Gly Arg
1               5                   10                  15

<210> SEQ ID NO 12
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="peptide"
      /organism="Artificial Sequence"
<220> FEATURE:
<221> NAME/KEY: MOD_RES
<222> LOCATION: 7..7
```

```
<223> OTHER INFORMATION: PHOSPHORYLATION

<400> SEQUENCE: 12

Lys Lys Ser Arg Gly Asp Tyr Met Thr Met Gln Ile Gly
1               5                   10

<210> SEQ ID NO 13
<211> LENGTH: 13
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="peptide"
      /organism="Artificial Sequence"
<220> FEATURE:
<221> NAME/KEY: MOD_RES
<222> LOCATION: 7..7
<223> OTHER INFORMATION: PHOSPHORYLATION

<400> SEQUENCE: 13

Lys Lys Ser Arg Gly Asn Tyr Met Thr Met Gln Ile Gly
1               5                   10

<210> SEQ ID NO 14
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"
<220> FEATURE:
<221> NAME/KEY: MOD_RES
<222> LOCATION: 2..2
<223> OTHER INFORMATION: PHOSPHORYLATION
<220> FEATURE:
<221> NAME/KEY: SITE
<222> LOCATION: 3..3
<223> OTHER INFORMATION: X is M or Nle
<220> FEATURE:
<221> NAME/KEY: SITE
<222> LOCATION: 5..5
<223> OTHER INFORMATION: X is M or Nle

<400> SEQUENCE: 14

Gly Tyr Xaa Pro Xaa Ser
1               5

<210> SEQ ID NO 15
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"
<220> FEATURE:
<221> NAME/KEY: MOD_RES
<222> LOCATION: 2..2
<223> OTHER INFORMATION: PHOSPHORYLATION
<220> FEATURE:
<221> NAME/KEY: SITE
<222> LOCATION: 3..3
<223> OTHER INFORMATION: X is M or Nle
<220> FEATURE:
<221> NAME/KEY: SITE
<222> LOCATION: 5..5
```

```
<223> OTHER INFORMATION: X is M or Nle

<400> SEQUENCE: 15

Gly Tyr Xaa Phe Xaa Ser
1               5

<210> SEQ ID NO 16
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"
<220> FEATURE:
<221> NAME/KEY: MOD_RES
<222> LOCATION: 2..2
<223> OTHER INFORMATION: PHOSPHORYLATION
<220> FEATURE:
<221> NAME/KEY: SITE
<222> LOCATION: 3..3
<223> OTHER INFORMATION: X is M or Nle
<220> FEATURE:
<221> NAME/KEY: SITE
<222> LOCATION: 5..5
<223> OTHER INFORMATION: X is M or Nle

<400> SEQUENCE: 16

Asp Tyr Xaa Pro Xaa Ser
1               5

<210> SEQ ID NO 17
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"
<220> FEATURE:
<221> NAME/KEY: MOD_RES
<222> LOCATION: 2..2
<223> OTHER INFORMATION: PHOSPHORYLATION
<220> FEATURE:
<221> NAME/KEY: SITE
<222> LOCATION: 3..3
<223> OTHER INFORMATION: X is M or Nle
<220> FEATURE:
<221> NAME/KEY: SITE
<222> LOCATION: 5..5
<223> OTHER INFORMATION: X is M or Nle

<400> SEQUENCE: 17

Gly Tyr Xaa Met Xaa Ser
1               5

<210> SEQ ID NO 18
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"
<220> FEATURE:
<221> NAME/KEY: MOD_RES
<222> LOCATION: 2..2
```

```
<223> OTHER INFORMATION: PHOSPHORYLATION
<220> FEATURE:
<221> NAME/KEY: SITE
<222> LOCATION: 3..3
<223> OTHER INFORMATION: X is M or Nle
<220> FEATURE:
<221> NAME/KEY: SITE
<222> LOCATION: 5..5
<223> OTHER INFORMATION: X is M or Nle

<400> SEQUENCE: 18

Asp Tyr Xaa Asn Xaa Ser
1               5

<210> SEQ ID NO 19
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"
<220> FEATURE:
<221> NAME/KEY: MOD_RES
<222> LOCATION: 2..2
<223> OTHER INFORMATION: PHOSPHORYLATION
<220> FEATURE:
<221> NAME/KEY: SITE
<222> LOCATION: 3..3
<223> OTHER INFORMATION: X is M or Nle
<220> FEATURE:
<221> NAME/KEY: SITE
<222> LOCATION: 5..5
<223> OTHER INFORMATION: X is M or Nle

<400> SEQUENCE: 19

Glu Tyr Xaa Asn Xaa Asp
1               5

<210> SEQ ID NO 20
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"
<220> FEATURE:
<221> NAME/KEY: MOD_RES
<222> LOCATION: 2..2
<223> OTHER INFORMATION: PHOSPHORYLATION
<220> FEATURE:
<221> NAME/KEY: SITE
<222> LOCATION: 3..3
<223> OTHER INFORMATION: X is M or Nle
<220> FEATURE:
<221> NAME/KEY: SITE
<222> LOCATION: 5..5
<223> OTHER INFORMATION: X is M or Nle

<400> SEQUENCE: 20

Asp Tyr Xaa Thr Xaa Gln
1               5

<210> SEQ ID NO 21
<211> LENGTH: 30
<212> TYPE: PRT
<213> ORGANISM: Artificial Sequence
<220> FEATURE:
```

```
<221> NAME/KEY: SOURCE
<222> LOCATION: 1..30
<223> OTHER INFORMATION: /mol_type="protein"
      /note="peptide"
      /organism="Artificial Sequence"
<220> FEATURE:
<221> NAME/KEY: MOD_RES
<222> LOCATION: 12..12
<223> OTHER INFORMATION: PHOSPHORYLATION
<220> FEATURE:
<221> NAME/KEY: SITE
<222> LOCATION: 13..13
<223> OTHER INFORMATION: X is M or Nle
<220> FEATURE:
<221> NAME/KEY: SITE
<222> LOCATION: 15..15
<223> OTHER INFORMATION: X is M or Nle

<400> SEQUENCE: 21

Pro Asp Ser Ser Thr Leu His Thr Asp Asp Gly Tyr Xaa Pro Xaa Ser
1               5                   10                  15

Pro Gly Val Ala Pro Val Pro Ser Gly Arg Lys Gly Ser Gly
            20                  25                  30

<210> SEQ ID NO 22
<211> LENGTH: 30
<212> TYPE: PRT
<213> ORGANISM: Artificial Sequence
<220> FEATURE:
<221> NAME/KEY: SOURCE
<222> LOCATION: 1..30
<223> OTHER INFORMATION: /mol_type="protein"
      /note="peptide"
      /organism="Artificial Sequence"
<220> FEATURE:
<221> NAME/KEY: MOD_RES
<222> LOCATION: 12..12
<223> OTHER INFORMATION: PHOSPHORYLATION
<220> FEATURE:
<221> NAME/KEY: SITE
<222> LOCATION: 13..13
<223> OTHER INFORMATION: X is M or Nle
<220> FEATURE:
<221> NAME/KEY: SITE
<222> LOCATION: 15..15
<223> OTHER INFORMATION: X is M or Nle

<400> SEQUENCE: 22

Pro Asp Ser Ser Thr Leu His Thr Asp Asp Gly Tyr Xaa Phe Xaa Ser
1               5                   10                  15

Pro Gly Val Ala Pro Val Pro Ser Gly Arg Lys Gly Ser Gly
            20                  25                  30

<210> SEQ ID NO 23
<211> LENGTH: 30
<212> TYPE: PRT
<213> ORGANISM: Artificial Sequence
<220> FEATURE:
<221> NAME/KEY: SOURCE
<222> LOCATION: 1..30
<223> OTHER INFORMATION: /mol_type="protein"
      /note="peptide"
      /organism="Artificial Sequence"
<220> FEATURE:
<221> NAME/KEY: MOD_RES
<222> LOCATION: 12..12
<223> OTHER INFORMATION: PHOSPHORYLATION
<220> FEATURE:
<221> NAME/KEY: SITE
<222> LOCATION: 13..13
<223> OTHER INFORMATION: X is M or Nle
<220> FEATURE:
<221> NAME/KEY: SITE
```

<222> LOCATION: 15..15
<223> OTHER INFORMATION: X is M or Nle

<400> SEQUENCE: 23

Pro Val Pro Ser Gly Arg Lys Gly Ser Gly Asp Tyr Xaa Pro Xaa Ser
1               5                   10                  15

Pro Lys Ser Val Ser Ala Pro Gln Gln Ile Ile Asn Pro Ile
            20                  25                  30

<210> SEQ ID NO 24
<211> LENGTH: 30
<212> TYPE: PRT
<213> ORGANISM: Artificial Sequence
<220> FEATURE:
<221> NAME/KEY: SOURCE
<222> LOCATION: 1..30
<223> OTHER INFORMATION: /mol_type="protein"
      /note="peptide"
      /organism="Artificial Sequence"
<220> FEATURE:
<221> NAME/KEY: MOD_RES
<222> LOCATION: 12..12
<223> OTHER INFORMATION: PHOSPHORYLATION
<220> FEATURE:
<221> NAME/KEY: SITE
<222> LOCATION: 13..13
<223> OTHER INFORMATION: X is M or Nle
<220> FEATURE:
<221> NAME/KEY: SITE
<222> LOCATION: 15..15
<223> OTHER INFORMATION: X is M or Nle

<400> SEQUENCE: 24

Arg Arg His Pro Gln Arg Val Asp Pro Asn Gly Tyr Xaa Met Xaa Ser
1               5                   10                  15

Pro Ser Gly Gly Cys Ser Pro Asp Ile Gly Gly Gly Pro Ser
            20                  25                  30

<210> SEQ ID NO 25
<211> LENGTH: 30
<212> TYPE: PRT
<213> ORGANISM: Artificial Sequence
<220> FEATURE:
<221> NAME/KEY: SOURCE
<222> LOCATION: 1..30
<223> OTHER INFORMATION: /mol_type="protein"
      /note="peptide"
      /organism="Artificial Sequence"
<220> FEATURE:
<221> NAME/KEY: MOD_RES
<222> LOCATION: 12..12
<223> OTHER INFORMATION: PHOSPHORYLATION
<220> FEATURE:
<221> NAME/KEY: SITE
<222> LOCATION: 13..13
<223> OTHER INFORMATION: X is M or Nle
<220> FEATURE:
<221> NAME/KEY: SITE
<222> LOCATION: 15..15
<223> OTHER INFORMATION: X is M or Nle

<400> SEQUENCE: 25

Ser Gly Gly Lys Leu Leu Pro Cys Thr Gly Asp Tyr Xaa Asn Xaa Ser
1               5                   10                  15

Pro Val Gly Asp Ser Asn Thr Ser Ser Pro Ser Asp Cys Tyr
            20                  25                  30

<210> SEQ ID NO 26
<211> LENGTH: 30
<212> TYPE: PRT

```
<213> ORGANISM: Artificial Sequence
<220> FEATURE:
<221> NAME/KEY: SOURCE
<222> LOCATION: 1..30
<223> OTHER INFORMATION: /mol_type="protein"
      /note="peptide"
      /organism="Artificial Sequence"
<220> FEATURE:
<221> NAME/KEY: MOD_RES
<222> LOCATION: 11..11
<223> OTHER INFORMATION: PHOSPHORYLATION
<220> FEATURE:
<221> NAME/KEY: SITE
<222> LOCATION: 12..12
<223> OTHER INFORMATION: X is M or Nle
<220> FEATURE:
<221> NAME/KEY: SITE
<222> LOCATION: 14..14
<223> OTHER INFORMATION: X is M or Nle

<400> SEQUENCE: 26

Pro Arg Glu Glu Glu Thr Gly Thr Glu Glu Tyr Xaa Lys Xaa Asp Leu
1               5                   10                  15

Gly Pro Gly Arg Arg Ala Ala Trp Gln Glu Ser Thr Gly Val
            20                  25                  30

<210> SEQ ID NO 27
<211> LENGTH: 30
<212> TYPE: PRT
<213> ORGANISM: Artificial Sequence
<220> FEATURE:
<221> NAME/KEY: SOURCE
<222> LOCATION: 1..30
<223> OTHER INFORMATION: /mol_type="protein"
      /note="peptide"
      /organism="Artificial Sequence"
<220> FEATURE:
<221> NAME/KEY: MOD_RES
<222> LOCATION: 11..11
<223> OTHER INFORMATION: PHOSPHORYLATION
<220> FEATURE:
<221> NAME/KEY: SITE
<222> LOCATION: 12..12
<223> OTHER INFORMATION: X is M or Nle
<220> FEATURE:
<221> NAME/KEY: SITE
<222> LOCATION: 14..14
<223> OTHER INFORMATION: X is M or Nle

<400> SEQUENCE: 27

Pro Arg Glu Glu Glu Thr Gly Thr Glu Glu Tyr Xaa Asn Xaa Asp Leu
1               5                   10                  15

Gly Pro Gly Arg Arg Ala Ala Trp Gln Glu Ser Thr Gly Val
            20                  25                  30

<210> SEQ ID NO 28
<211> LENGTH: 30
<212> TYPE: PRT
<213> ORGANISM: Artificial Sequence
<220> FEATURE:
<221> NAME/KEY: SOURCE
<222> LOCATION: 1..30
<223> OTHER INFORMATION: /mol_type="protein"
      /note="peptide"
      /organism="Artificial Sequence"
<220> FEATURE:
<221> NAME/KEY: MOD_RES
<222> LOCATION: 9..9
<223> OTHER INFORMATION: PHOSPHORYLATION
<220> FEATURE:
<221> NAME/KEY: SITE
<222> LOCATION: 10..10
<223> OTHER INFORMATION: X is M or Nle
```

```
<220> FEATURE:
<221> NAME/KEY: SITE
<222> LOCATION: 12..12
<223> OTHER INFORMATION: X is M or Nle

<400> SEQUENCE: 28

Ala Val Pro Ser Ser Arg Gly Asp Tyr Xaa Thr Xaa Gln Met Ser Cys
1               5                   10                  15

Pro Arg Gln Ser Tyr Val Asp Thr Ser Pro Ala Ala Pro Val
            20                  25                  30

<210> SEQ ID NO 29
<211> LENGTH: 11
<212> TYPE: PRT
<213> ORGANISM: Artificial Sequence
<220> FEATURE:
<221> NAME/KEY: SOURCE
<222> LOCATION: 1..11
<223> OTHER INFORMATION: /mol_type="protein"
      /note="peptide"
      /organism="Artificial Sequence"
<220> FEATURE:
<221> NAME/KEY: MOD_RES
<222> LOCATION: 6..6
<223> OTHER INFORMATION: PHOSPHORYLATION

<400> SEQUENCE: 29

Glu Glu Glu Tyr Met Pro Met Glu Asp Leu Tyr
1               5                   10

<210> SEQ ID NO 30
<211> LENGTH: 11
<212> TYPE: PRT
<213> ORGANISM: Artificial Sequence
<220> FEATURE:
<221> NAME/KEY: SOURCE
<222> LOCATION: 1..11
<223> OTHER INFORMATION: /mol_type="protein"
      /note="peptide"
      /organism="Artificial Sequence"
<220> FEATURE:
<221> NAME/KEY: MOD_RES
<222> LOCATION: 4..4
<223> OTHER INFORMATION: PHOSPHORYLATION

<400> SEQUENCE: 30

Asp Gly Gly Tyr Met Asp Met Ser Lys Asp Glu
1               5                   10

<210> SEQ ID NO 31
<211> LENGTH: 16
<212> TYPE: PRT
<213> ORGANISM: Artificial Sequence
<220> FEATURE:
<221> NAME/KEY: SOURCE
<222> LOCATION: 1..16
<223> OTHER INFORMATION: /mol_type="protein"
      /note="peptide"
      /organism="Artificial Sequence"
<220> FEATURE:
<221> NAME/KEY: MOD_RES
<222> LOCATION: 10..10
<223> OTHER INFORMATION: PHOSPHORYLATION

<400> SEQUENCE: 31

Lys Lys Lys Glu Glu Glu Glu Glu Tyr Met Pro Met Glu Asp Leu
1               5                   10                  15

<210> SEQ ID NO 32
<211> LENGTH: 13
```

```
<212> TYPE: PRT
<213> ORGANISM: Artificial Sequence
<220> FEATURE:
<221> NAME/KEY: SOURCE
<222> LOCATION: 1..13
<223> OTHER INFORMATION: /mol_type="protein"
      /note="peptide"
      /organism="Artificial Sequence"
<220> FEATURE:
<221> NAME/KEY: MOD_RES
<222> LOCATION: 7..7
<223> OTHER INFORMATION: PHOSPHORYLATION
<220> FEATURE:
<221> NAME/KEY: MOD_RES
<222> LOCATION: 8..8
<223> OTHER INFORMATION: Nle

<400> SEQUENCE: 32

Lys Lys Ser Arg Gly Asp Tyr Xaa Thr Met Gln Ile Gly
1               5                   10

<210> SEQ ID NO 33
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"
<220> FEATURE:
<221> NAME/KEY: MOD_RES
<222> LOCATION: 2..2
<223> OTHER INFORMATION: PHOSPHORYLATION
<220> FEATURE:
<221> NAME/KEY: SITE
<222> LOCATION: 3..3
<223> OTHER INFORMATION: X is M or Nle
<220> FEATURE:
<221> NAME/KEY: SITE
<222> LOCATION: 4..4
<223> OTHER INFORMATION: X is P, F or M
<220> FEATURE:
<221> NAME/KEY: SITE
<222> LOCATION: 5..5
<223> OTHER INFORMATION: X is M or Nle

<400> SEQUENCE: 33

Gly Tyr Xaa Xaa Xaa Ser
1               5

<210> SEQ ID NO 34
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"
<220> FEATURE:
<221> NAME/KEY: MOD_RES
<222> LOCATION: 2..2
<223> OTHER INFORMATION: PHOSPHORYLATION
<220> FEATURE:
<221> NAME/KEY: SITE
<222> LOCATION: 3..3
<223> OTHER INFORMATION: X is M or Nle
<220> FEATURE:
<221> NAME/KEY: SITE
<222> LOCATION: 4..4
<223> OTHER INFORMATION: X is P or N
<220> FEATURE:
```

```
<221> NAME/KEY: SITE
<222> LOCATION: 5..5
<223> OTHER INFORMATION: X is M or Nle

<400> SEQUENCE: 34

Asp Tyr Xaa Xaa Xaa Ser
1               5

<210> SEQ ID NO 35
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"
<220> FEATURE:
<221> NAME/KEY: MOD_RES
<222> LOCATION: 2..2
<223> OTHER INFORMATION: PHOSPHORYLATION
<220> FEATURE:
<221> NAME/KEY: SITE
<222> LOCATION: 3..3
<223> OTHER INFORMATION: X is M or Nle
<220> FEATURE:
<221> NAME/KEY: SITE
<222> LOCATION: 5..5
<223> OTHER INFORMATION: X is M or Nle

<400> SEQUENCE: 35

Glu Tyr Xaa Asn Xaa Asp
1               5

<210> SEQ ID NO 36
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"
<220> FEATURE:
<221> NAME/KEY: MOD_RES
<222> LOCATION: 2..2
<223> OTHER INFORMATION: PHOSPHORYLATION
<220> FEATURE:
<221> NAME/KEY: SITE
<222> LOCATION: 3..3
<223> OTHER INFORMATION: X is M or Nle
<220> FEATURE:
<221> NAME/KEY: SITE
<222> LOCATION: 5..5
<223> OTHER INFORMATION: X is M or Nle

<400> SEQUENCE: 36

Asp Tyr Xaa Thr Xaa Gln
1               5

<210> SEQ ID NO 37
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"
<220> FEATURE:
```

```
<221> NAME/KEY: MOD_RES
<222> LOCATION: 2..2
<223> OTHER INFORMATION: PHOSPHORYLATION

<400> SEQUENCE: 37

Gly Tyr Met Phe Met Ser
1               5

<210> SEQ ID NO 38
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"
<220> FEATURE:
<221> NAME/KEY: MOD_RES
<222> LOCATION: 2..2
<223> OTHER INFORMATION: PHOSPHORYLATION

<400> SEQUENCE: 38

Glu Tyr Met Asn Met Asp
1               5

<210> SEQ ID NO 39
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"
<220> FEATURE:
<221> NAME/KEY: MOD_RES
<222> LOCATION: 2..2
<223> OTHER INFORMATION: PHOSPHORYLATION

<400> SEQUENCE: 39

Asp Tyr Met Thr Met Gln
1               5

<210> SEQ ID NO 40
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide"
      /organism="Artificial Sequence"

<400> SEQUENCE: 40

Asn Tyr Ile Cys Met Gly
1               5

<210> SEQ ID NO 41
<211> LENGTH: 12
<212> TYPE: PRT
<213> ORGANISM: artificial sequences
<220> FEATURE:
<221> NAME/KEY: SOURCE
<222> LOCATION: 1..12
<223> OTHER INFORMATION: /mol_type="protein"
      /note="peptide"
      /organism="artificial sequences"
```

```
<220> FEATURE:
<221> NAME/KEY: MOD_RES
<222> LOCATION: 5
<223> OTHER INFORMATION: PHOSPHORYLATION

<400> SEQUENCE: 41

Thr Asp Asp Gly Tyr Met Pro Met Ser Pro Gly Val
1               5                   10

<210> SEQ ID NO 42
<211> LENGTH: 12
<212> TYPE: PRT
<213> ORGANISM: artificial sequences
<220> FEATURE:
<221> NAME/KEY: SOURCE
<222> LOCATION: 1..12
<223> OTHER INFORMATION: /mol_type="protein"
      /note="peptide"
      /organism="artificial sequences"
<220> FEATURE:
<221> NAME/KEY: MOD_RES
<222> LOCATION: 5
<223> OTHER INFORMATION: PHOSPHORYLATION

<400> SEQUENCE: 42

Gly Asn Gly Asp Tyr Met Pro Met Asp Pro Lys Ser
1               5                   10

<210> SEQ ID NO 43
<211> LENGTH: 12
<212> TYPE: PRT
<213> ORGANISM: artificial sequences
<220> FEATURE:
<221> NAME/KEY: SOURCE
<222> LOCATION: 1..12
<223> OTHER INFORMATION: /mol_type="protein"
      /note="peptide"
      /organism="artificial sequences"
<220> FEATURE:
<221> NAME/KEY: MOD_RES
<222> LOCATION: 5
<223> OTHER INFORMATION: PHOSPHORYLATION

<400> SEQUENCE: 43

Asp Pro Asn Gly Tyr Met Met Met Ser Pro Ser Gly
1               5                   10

<210> SEQ ID NO 44
<211> LENGTH: 12
<212> TYPE: PRT
<213> ORGANISM: artificial sequences
<220> FEATURE:
<221> NAME/KEY: SOURCE
<222> LOCATION: 1..12
<223> OTHER INFORMATION: /mol_type="protein"
      /note="peptide"
      /organism="artificial sequences"
<220> FEATURE:
<221> NAME/KEY: MOD_RES
<222> LOCATION: 5
<223> OTHER INFORMATION: PHOSPHORYLATION

<400> SEQUENCE: 44

Gly Asn Gly Asp Tyr Met Pro Met Ser Pro Lys Ser
1               5                   10

<210> SEQ ID NO 45
<211> LENGTH: 13
<212> TYPE: PRT
<213> ORGANISM: artificial sequences
<220> FEATURE:
```

```
<221> NAME/KEY: SOURCE
<222> LOCATION: 1..13
<223> OTHER INFORMATION: /mol_type="protein"
      /note="peptide"
      /organism="artificial sequences"
<220> FEATURE:
<221> NAME/KEY: MOD_RES
<222> LOCATION: 5
<223> OTHER INFORMATION: PHOSPHORYLATION

<400> SEQUENCE: 45

Arg Glu Asn Glu Tyr Met Pro Met Ala Pro Gln Ile His
1               5                   10

<210> SEQ ID NO 46
<211> LENGTH: 13
<212> TYPE: PRT
<213> ORGANISM: artificial sequences
<220> FEATURE:
<221> NAME/KEY: SOURCE
<222> LOCATION: 1..13
<223> OTHER INFORMATION: /mol_type="protein"
      /note="peptide"
      /organism="artificial sequences"
<220> FEATURE:
<221> NAME/KEY: MOD_RES
<222> LOCATION: 5
<223> OTHER INFORMATION: PHOSPHORYLATION

<400> SEQUENCE: 46

Glu Glu Glu Glu Tyr Met Pro Met Glu Asp Leu Tyr Leu
1               5                   10

<210> SEQ ID NO 47
<211> LENGTH: 13
<212> TYPE: PRT
<213> ORGANISM: artificial sequences
<220> FEATURE:
<221> NAME/KEY: SOURCE
<222> LOCATION: 1..13
<223> OTHER INFORMATION: /mol_type="protein"
      /note="peptide"
      /organism="artificial sequences"
<220> FEATURE:
<221> NAME/KEY: MOD_RES
<222> LOCATION: 5
<223> OTHER INFORMATION: PHOSPHORYLATION

<400> SEQUENCE: 47

Thr Asp Asp Gly Tyr Met Pro Met Ser Pro Gly Val Ala
1               5                   10

<210> SEQ ID NO 48
<211> LENGTH: 13
<212> TYPE: PRT
<213> ORGANISM: artificial sequences
<220> FEATURE:
<221> NAME/KEY: SOURCE
<222> LOCATION: 1..13
<223> OTHER INFORMATION: /mol_type="protein"
      /note="peptide"
      /organism="artificial sequences"
<220> FEATURE:
<221> NAME/KEY: MOD_RES
<222> LOCATION: 5
<223> OTHER INFORMATION: PHOSPHORYLATION

<400> SEQUENCE: 48

Gly Asn Gly Asp Tyr Met Pro Met Ser Pro Lys Ser Val
1               5                   10
```

```
<210> SEQ ID NO 49
<211> LENGTH: 13
<212> TYPE: PRT
<213> ORGANISM: artificial sequences
<220> FEATURE:
<221> NAME/KEY: SOURCE
<222> LOCATION: 1..13
<223> OTHER INFORMATION: /mol_type="protein"
      /note="peptide"
      /organism="artificial sequences"
<220> FEATURE:
<221> NAME/KEY: MOD_RES
<222> LOCATION: 5
<223> OTHER INFORMATION: PHOSPHORYLATION

<400> SEQUENCE: 49

Ser Asp Gly Gly Tyr Met Asp Met Ser Lys Asp Glu Ser
1               5                   10

<210> SEQ ID NO 50
<211> LENGTH: 10
<212> TYPE: PRT
<213> ORGANISM: artificial sequences
<220> FEATURE:
<221> NAME/KEY: SOURCE
<222> LOCATION: 1..10
<223> OTHER INFORMATION: /mol_type="protein"
      /note="peptide"
      /organism="artificial sequences"
<220> FEATURE:
<221> NAME/KEY: MOD_RES
<222> LOCATION: 4
<223> OTHER INFORMATION: PHOSPHORYLATION

<400> SEQUENCE: 50

Arg Asp Gly Tyr Met Thr Met Gln Ile Gly
1               5                   10

<210> SEQ ID NO 51
<211> LENGTH: 9
<212> TYPE: PRT
<213> ORGANISM: artificial sequences
<220> FEATURE:
<221> NAME/KEY: SOURCE
<222> LOCATION: 1..9
<223> OTHER INFORMATION: /mol_type="protein"
      /note="peptide"
      /organism="artificial sequences"
<220> FEATURE:
<221> NAME/KEY: MOD_RES
<222> LOCATION: 4
<223> OTHER INFORMATION: PHOSPHORYLATION

<400> SEQUENCE: 51

Ile Asp Val Tyr Met Ile Met Val Lys
1               5

<210> SEQ ID NO 52
<211> LENGTH: 11
<212> TYPE: PRT
<213> ORGANISM: artificial sequences
<220> FEATURE:
<221> NAME/KEY: SOURCE
<222> LOCATION: 1..11
<223> OTHER INFORMATION: /mol_type="protein"
      /note="peptide"
      /organism="artificial sequences"
<220> FEATURE:
<221> NAME/KEY: MOD_RES
<222> LOCATION: 4
<223> OTHER INFORMATION: PHOSPHORYLATION

<400> SEQUENCE: 52
```

```
Asp Gly Gly Tyr Met Asp Met Ser Lys Asp Glu
1               5                   10

<210> SEQ ID NO 53
<211> LENGTH: 10
<212> TYPE: PRT
<213> ORGANISM: artificial sequences
<220> FEATURE:
<221> NAME/KEY: SOURCE
<222> LOCATION: 1..10
<223> OTHER INFORMATION: /mol_type="protein"
      /note="peptide"
      /organism="artificial sequences"
<220> FEATURE:
<221> NAME/KEY: MOD_RES
<222> LOCATION: 4
<223> OTHER INFORMATION: PHOSPHORYLATION

<400> SEQUENCE: 53

His Ser Asp Tyr Met Asn Met Thr Pro Arg
1               5                   10

<210> SEQ ID NO 54
<211> LENGTH: 11
<212> TYPE: PRT
<213> ORGANISM: artificial sequences
<220> FEATURE:
<221> NAME/KEY: SOURCE
<222> LOCATION: 1..11
<223> OTHER INFORMATION: /mol_type="protein"
      /note="peptide"
      /organism="artificial sequences"
<220> FEATURE:
<221> NAME/KEY: MOD_RES
<222> LOCATION: 4
<223> OTHER INFORMATION: PHOSPHORYLATION

<400> SEQUENCE: 54

Asn Gly Asp Tyr Met Pro Met Ser Pro Lys Ser
1               5                   10

<210> SEQ ID NO 55
<211> LENGTH: 10
<212> TYPE: PRT
<213> ORGANISM: artificial sequences
<220> FEATURE:
<221> NAME/KEY: SOURCE
<222> LOCATION: 1..10
<223> OTHER INFORMATION: /mol_type="protein"
      /note="peptide"
      /organism="artificial sequences"
<220> FEATURE:
<221> NAME/KEY: MOD_RES
<222> LOCATION: 3
<223> OTHER INFORMATION: PHOSPHORYLATION

<400> SEQUENCE: 55

Gly Asp Tyr Met Pro Met Ser Pro Lys Ser
1               5                   10

<210> SEQ ID NO 56
<211> LENGTH: 9
<212> TYPE: PRT
<213> ORGANISM: artificial sequences
<220> FEATURE:
<221> NAME/KEY: SOURCE
<222> LOCATION: 1..9
<223> OTHER INFORMATION: /mol_type="protein"
      /note="peptide"
      /organism="artificial sequences"
<220> FEATURE:
```

```
<221> NAME/KEY: MOD_RES
<222> LOCATION: 2
<223> OTHER INFORMATION: PHOSPHORYLATION

<400> SEQUENCE: 56

Asp Tyr Met Pro Met Ser Pro Lys Ser
1               5

<210> SEQ ID NO 57
<211> LENGTH: 8
<212> TYPE: PRT
<213> ORGANISM: artificial sequences
<220> FEATURE:
<221> NAME/KEY: SOURCE
<222> LOCATION: 1..8
<223> OTHER INFORMATION: /mol_type="protein"
      /note="peptide"
      /organism="artificial sequences"
<220> FEATURE:
<221> NAME/KEY: MOD_RES
<222> LOCATION: 1
<223> OTHER INFORMATION: PHOSPHORYLATION

<400> SEQUENCE: 57

Tyr Met Pro Met Ser Pro Lys Ser
1               5

<210> SEQ ID NO 58
<211> LENGTH: 6
<212> TYPE: PRT
<213> ORGANISM: artificial sequences
<220> FEATURE:
<221> NAME/KEY: SOURCE
<222> LOCATION: 1..6
<223> OTHER INFORMATION: /mol_type="protein"
      /note="peptide"
      /organism="artificial sequences"
<220> FEATURE:
<221> NAME/KEY: MOD_RES
<222> LOCATION: 1
<223> OTHER INFORMATION: PHOSPHORYLATION

<400> SEQUENCE: 58

Tyr Met Pro Met Ser Pro
1               5

<210> SEQ ID NO 59
<211> LENGTH: 5
<212> TYPE: PRT
<213> ORGANISM: artificial sequences
<220> FEATURE:
<221> NAME/KEY: SOURCE
<222> LOCATION: 1..5
<223> OTHER INFORMATION: /mol_type="protein"
      /note="peptide"
      /organism="artificial sequences"
<220> FEATURE:
<221> NAME/KEY: MOD_RES
<222> LOCATION: 1
<223> OTHER INFORMATION: PHOSPHORYLATION

<400> SEQUENCE: 59

Tyr Met Pro Met Ser
1               5

<210> SEQ ID NO 60
<211> LENGTH: 4
<212> TYPE: PRT
<213> ORGANISM: artificial sequences
<220> FEATURE:
<221> NAME/KEY: SOURCE
```

```
-continued

<222> LOCATION: 1..4
<223> OTHER INFORMATION: /mol_type="protein"
      /note="peptide"
      /organism="artificial sequences"
<220> FEATURE:
<221> NAME/KEY: MOD_RES
<222> LOCATION: 1
<223> OTHER INFORMATION: PHOSPHORYLATION

<400> SEQUENCE: 60

Tyr Met Pro Met
1

<210> SEQ ID NO 61
<211> LENGTH: 8
<212> TYPE: PRT
<213> ORGANISM: artificial sequences
<220> FEATURE:
<221> NAME/KEY: SOURCE
<222> LOCATION: 1..8
<223> OTHER INFORMATION: /mol_type="protein"
      /note="peptide"
      /organism="artificial sequences"
<220> FEATURE:
<221> NAME/KEY: MOD_RES
<222> LOCATION: 1
<223> OTHER INFORMATION: PHOSPHORYLATION

<400> SEQUENCE: 61

Tyr Met Pro Met Ser Pro Ala Ser
1               5

<210> SEQ ID NO 62
<211> LENGTH: 8
<212> TYPE: PRT
<213> ORGANISM: artificial sequences
<220> FEATURE:
<221> NAME/KEY: SOURCE
<222> LOCATION: 1..8
<223> OTHER INFORMATION: /mol_type="protein"
      /note="peptide"
      /organism="artificial sequences"
<220> FEATURE:
<221> NAME/KEY: MOD_RES
<222> LOCATION: 1
<223> OTHER INFORMATION: PHOSPHORYLATION

<400> SEQUENCE: 62

Tyr Met Pro Met Ser Ala Lys Ser
1               5

<210> SEQ ID NO 63
<211> LENGTH: 8
<212> TYPE: PRT
<213> ORGANISM: artificial sequences
<220> FEATURE:
<221> NAME/KEY: SOURCE
<222> LOCATION: 1..8
<223> OTHER INFORMATION: /mol_type="protein"
      /note="peptide"
      /organism="artificial sequences"
<220> FEATURE:
<221> NAME/KEY: MOD_RES
<222> LOCATION: 1
<223> OTHER INFORMATION: PHOSPHORYLATION

<400> SEQUENCE: 63

Tyr Met Pro Met Ala Pro Lys Ser
1               5

<210> SEQ ID NO 64
```

```
<211> LENGTH: 8
<212> TYPE: PRT
<213> ORGANISM: artificial sequences
<220> FEATURE:
<221> NAME/KEY: SOURCE
<222> LOCATION: 1..8
<223> OTHER INFORMATION: /mol_type="protein"
      /note="peptide"
      /organism="artificial sequences"
<220> FEATURE:
<221> NAME/KEY: MOD_RES
<222> LOCATION: 1
<223> OTHER INFORMATION: PHOSPHORYLATION

<400> SEQUENCE: 64

Tyr Met Ala Met Ser Pro Lys Ser
1               5
```